United States Patent
Lin et al.

(10) Patent No.: US 11,884,640 B2
(45) Date of Patent: Jan. 30, 2024

(54) PROCESSES AND INTERMEDIATES FOR THE PREPARATIONS OF BENZOPROSTACYCLIN ANALOGUES AND BENZOPROSTACYCLIN ANALOGUES PREPARED THEREFROM

(71) Applicant: CHIROGATE INTERNATIONAL INC., Yangmei (TW)

(72) Inventors: Chun-Yu Lin, Yangmei (TW); Tzyh-Mann Wei, Yangmei (TW); Shih-Yi Wei, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 0 days.

(21) Appl. No.: 17/336,865

(22) Filed: Jun. 2, 2021

(65) Prior Publication Data

US 2023/0002339 A1 Jan. 5, 2023

(51) Int. Cl.
| | |
|---|---|
| *C07D 307/93* | (2006.01) |
| *C07C 45/65* | (2006.01) |
| *C07C 49/573* | (2006.01) |
| *C07C 67/24* | (2006.01) |
| *C07C 67/317* | (2006.01) |
| *C07C 69/157* | (2006.01) |
| *C07C 69/734* | (2006.01) |
| *C07D 307/42* | (2006.01) |
| *C07F 7/18* | (2006.01) |
| *C12P 7/38* | (2006.01) |

(52) U.S. Cl.
CPC ............ *C07D 307/93* (2013.01); *C07C 45/65* (2013.01); *C07C 49/573* (2013.01); *C07C 67/24* (2013.01); *C07C 67/317* (2013.01); *C07C 69/157* (2013.01); *C07C 69/734* (2013.01); *C07D 307/42* (2013.01); *C07F 7/1892* (2013.01); *C12P 7/38* (2013.01); *C07C 2601/08* (2017.05); *C07C 2601/10* (2017.05); *C07C 2601/16* (2017.05)

(58) Field of Classification Search
CPC .................................................... C07D 307/93
See application file for complete search history.

(56) References Cited

U.S. PATENT DOCUMENTS

| | | | |
|---|---|---|---|
| 5,202,447 A | 4/1993 | Ohno et al. | |
| 7,345,181 B2 | 3/2008 | Kim et al. | |
| 8,779,170 B2 | 7/2014 | Sharma et al. | |
| 9,334,255 B2 | 5/2016 | Sharma et al. | |
| 9,765,047 B2 | 9/2017 | Batra et al. | |

FOREIGN PATENT DOCUMENTS

| | | |
|---|---|---|
| CN | 106478572 | 3/2017 |
| JP | H07-238046 A | 9/1995 |
| JP | 2013-43890 A | 3/2013 |
| WO | 2017/174439 | 10/2017 |

OTHER PUBLICATIONS

Umemiya, Organic Letters (2017), 19(5), 1112-1115.*
CN 1064785727 _ English Translation.
Hiroshj Nagase, et al.: Synthesis of (+)-5,6,7-Trinor-4,8-Inter-m-Phenylene $PGI_2$1: Tetrahedron Lett. 1990, 31, 4493.
Shjgenobu Umemiya, et al.: Enantioselective total Synthesis of Beraprost using Organocatalyst; Org. Lett. 2017, 19, 1112.
Office Action issued from the JPO for the corresponding Japanese Patent Application 2022-85012.
Shigenobu Umemiya, et al.: Enantioselective Total Synthesis of Beraprost Using Organocatalyst, Organic Letters, 2017, 19(5), pp. 1112-1115.

* cited by examiner

*Primary Examiner* — Nizal S Chandrakumar
(74) *Attorney, Agent, or Firm* — LADAS & PARRY LLP

(57) ABSTRACT

The invention relates to processes for preparing benzoprostacyclin analogues and intermediates prepared from the process, and the benzoprostacyclin analogues prepared therefrom. The invention also relates to cyclopentenone intermediates in racemic or optically active form.

4 Claims, No Drawings

PROCESSES AND INTERMEDIATES FOR THE PREPARATIONS OF BENZOPROSTACYCLIN ANALOGUES AND BENZOPROSTACYCLIN ANALOGUES PREPARED THEREFROM

FIELD OF THE INVENTION

The present invention relates to novel processes and intermediates for the preparations of benzoprostacyclin analogues, and benzoprostacyclin analogues prepared therefrom.

BACKGROUND OF THE INVENTION

Since the discovery of prostacyclins, a number of chemically and metabolically stable benzoprostacyclin analogues have been developed as clinically effective antithrombotic agents. Among these, Beraprosts developed by Toray Industries Inc. are some of the most attractive compounds. The commercially available Beraprost Sodium is a racemic compound, i.e., a mixture of the following four isomers:

Beraprost Sodium

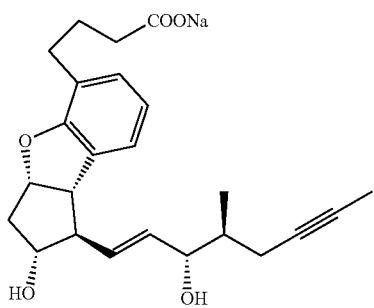

314d

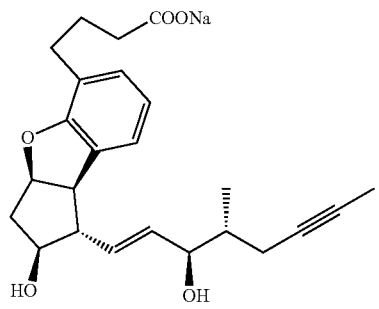

314l

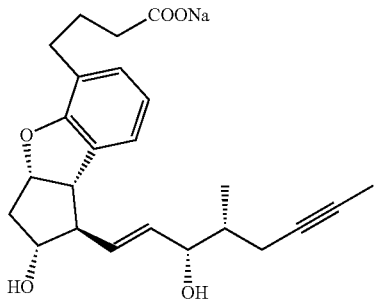

315d

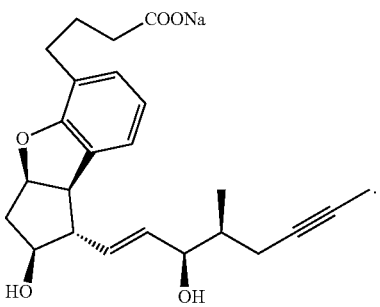

3151

Enantiomerically pure Beraprost-314d is a pharmacologically active isomer of Beraprost that is currently under clinical trials for the treatment of pulmonary hypertension and vascular diseases.

The syntheses of Beraprost or Beraprost-314d have been disclosed in the prior art, such as U.S. Pat. No. 5,202,447, CN106478572, WO2017/174439, U.S. Pat. No. 8,779,170, U.S. Pat. Nos. 9,334,255, 9,765,047, 8,779,170, *Tetrahedron Lett.* 1990, 31, 4493, and *Org. Lett.* 2017, 19, 1112, but they are linear and rather inefficient.

U.S. Pat. No. 7,345,181 discloses synthetic routes of Beraprost with higher efficiency by a conjugate addition reaction, as shown in the following Scheme A, which are started from a cyclopentenone $A_1$ via conjugate addition to form an intermediate $A_2$ (Step 1):

Scheme A

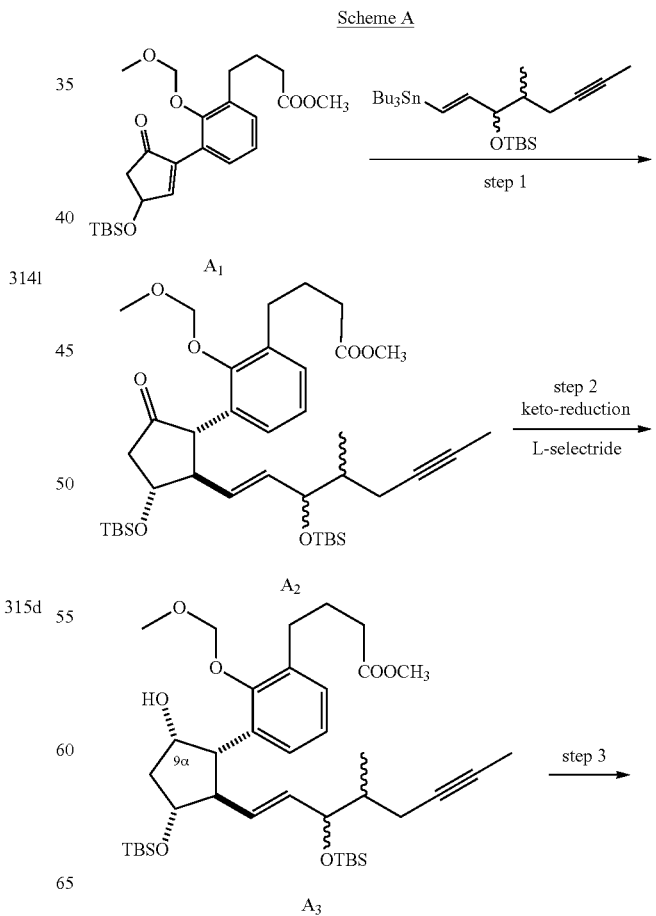

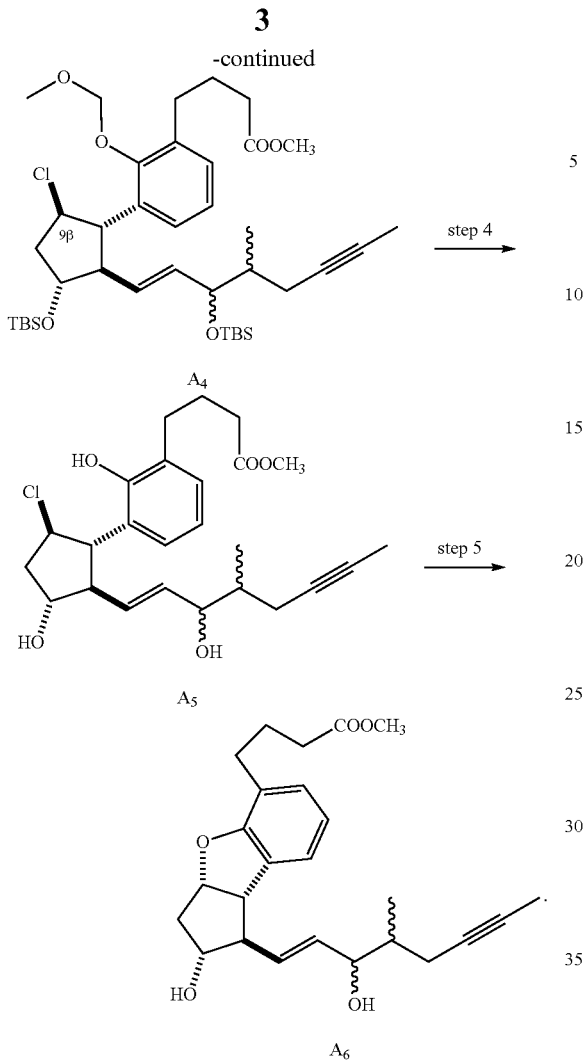

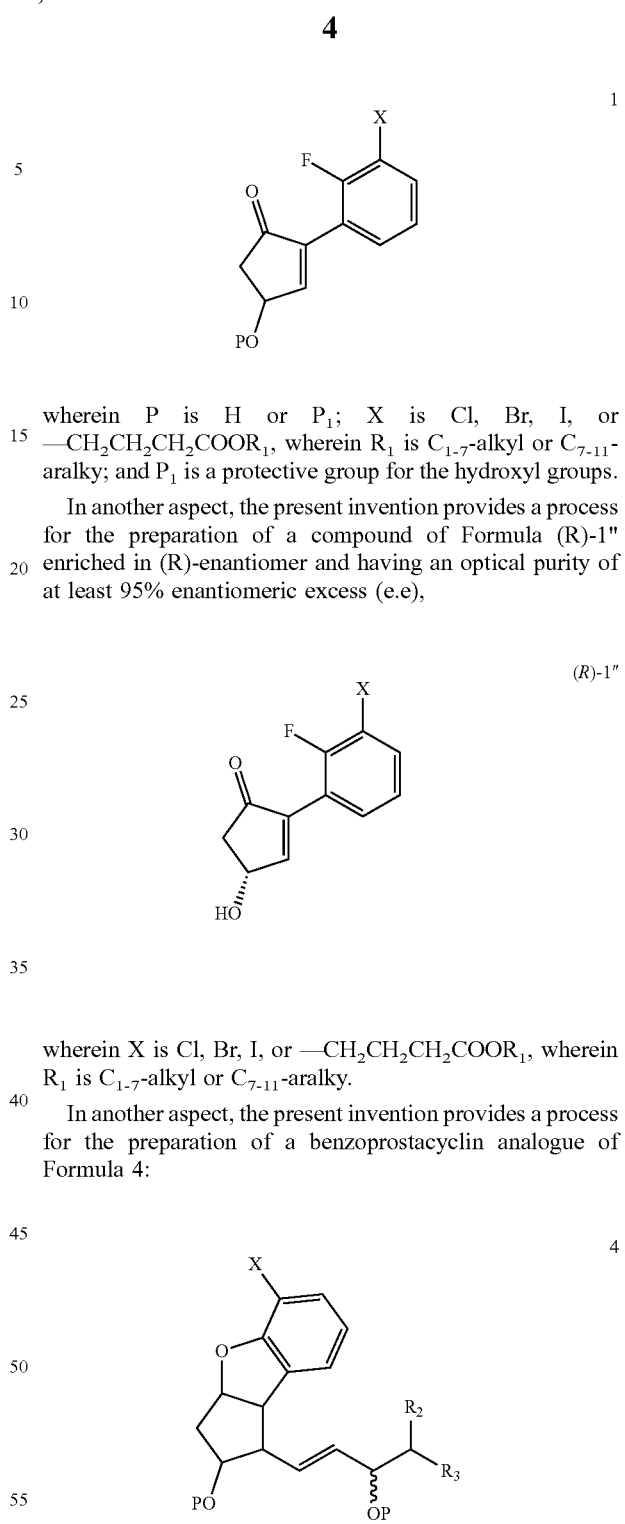

As shown in Scheme A, the intermediate $A_2$ having a 9-keto group reacts with L-selectride to obtain an intermediate $A_3$ having a 9α-hydroxyl group (Step 2). After that, the intermediate $A_3$ undergoes a $S_N2$ reaction to convert the 9α-hydroxyl group to a 9β-chloro group so as to form an intermediate $A_4$ (Step 3). Then, the intermediate $A_4$ is subjected to remove the methoxymethyl protecting group of phenol and the tert-butyldimethylsilyl protecting groups of hydroxyl (Step 4) and perform an intramolecular cyclization reaction to obtain an intermediate $A_6$ (Step 5).

However, this approach depicted in Scheme A requires at least five steps to form the tricyclic structure of benzoprostacyclin from the cyclopentenone $A_1$. There is therefore a need to discover and develop an efficient conjugate addition approach for forming the tricyclic structure of benzoprostacyclin in industry.

SUMMARY OF THE INVENTION

The objective of the present invention is to provide more efficient conjugate addition approaches for producing benzoprostacyclin analogues and intermediates thereof with higher diastereomeric and enantiomeric purity, thereby forming products with high purity.

In one aspect, the present invention provides a racemic or optically enriched cyclopentenone of Formula 1:

wherein P is H or $P_1$; X is Cl, Br, I, or —$CH_2CH_2CH_2COOR_1$, wherein $R_1$ is $C_{1-7}$-alkyl or $C_{7-11}$-aralky; and $P_1$ is a protective group for the hydroxyl groups.

In another aspect, the present invention provides a process for the preparation of a compound of Formula (R)-1" enriched in (R)-enantiomer and having an optical purity of at least 95% enantiomeric excess (e.e), wherein X is Cl, Br, I, or —$CH_2CH_2CH_2COOR_1$, wherein $R_1$ is $C_{1-7}$-alkyl or $C_{7-11}$-aralky.

In another aspect, the present invention provides a process for the preparation of a benzoprostacyclin analogue of Formula 4:

wherein P is H, $P_1$ or $P_2$; $R_2$ is H or $C_{1-4}$-alkyl; $R_3$ is $C_{1-7}$-alkyl, $C_{2-7}$-alkynyl, aryl, or aryloxy, each of which is unsubstituted or substituted by $C_{1-4}$-alkyl, halogen, or trihalomethyl; X is Cl, Br, I, or —$CH_2CH_2CH_2COOR_1$, wherein $R_1$ is $C_{1-7}$-alkyl or $C_{7-11}$-aralkyl; and $P_1$ or $P_2$ are protective groups for the hydroxyl groups.

In another aspect, the present invention provides a process for the preparation of an optically enriched benzoprostacyclin analogue of Formula 4a:

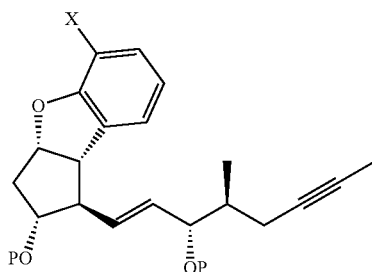

4a

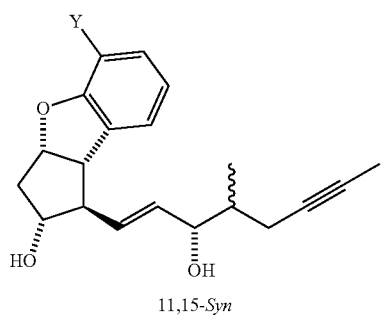

4b″

11,15-*Syn* wherein P is H, $P_1$ or $P_2$; X is Cl, Br, I, or —$CH_2CH_2CH_2COOR_1$, wherein $R_1$ is $C_{1-7}$-alkyl or $C_{7-11}$-aralkyl; and $P_1$ and $P_2$ are protective groups for the hydroxyl groups.

In one another aspect, the present invention provides a process for the preparation of a racemic benzoprostacyclin analogue of Formula 4b:

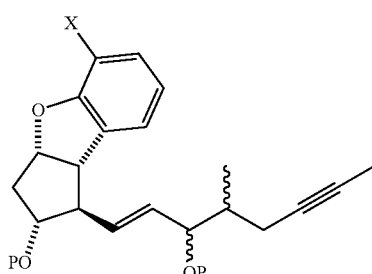

4b wherein P is H, $P_1$ or $P_2$; X is Cl, Br, I, or —$CH_2CH_2CH_2COOR_1$, wherein $R_1$ is $C_{1-7}$-alkyl or $C_{7-11}$-aralkyl; and $P_1$ and $P_2$ are protective groups for the hydroxyl groups.

In one another aspect, the present invention provides an optically enriched intermediate of Formula 4a″, wherein Y is Cl, Br, or I, which is used for the preparation of Beraprost-314d,

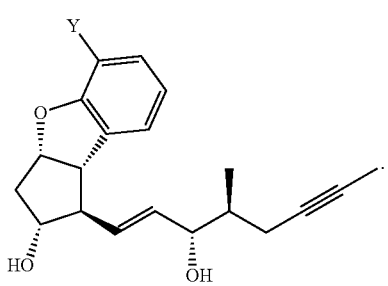

4a″

In yet another aspect, the present invention provides a racemic intermediate of Formula 11,15-Syn 4b″, wherein Y is Cl, Br, or I, which is used for the preparation of Beraprost, and at least comprises four isomers of Formula 4b″-1, Formula 4b″-2, Formula 4b″-3, and Formula 4b″-4:

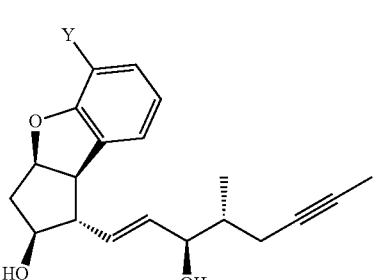

4b″-1

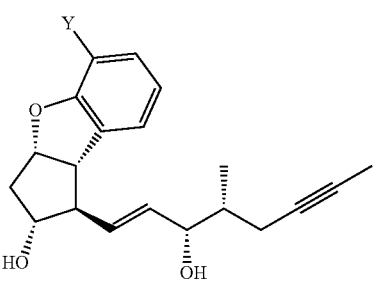

4b″-2

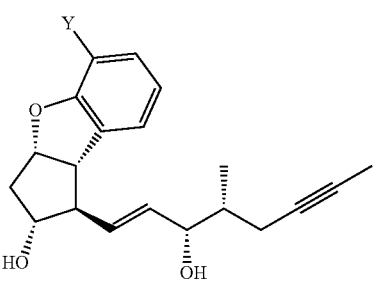

4b″-3

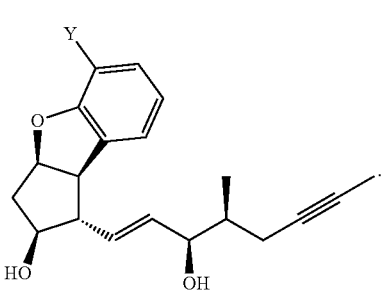

4b″-4

DETAILED DESCRIPTION OF THE INVENTION

Definition

The use of the word "a" or "an" when used in conjunction with the term "comprising" in the claims and/or the specification may mean "one," but is also consistent with the meaning of "one or more," "at least one," and "one or more than one." The use of the term "or" in the claims is used to mean "and/or" unless explicitly indicated to refer to alternatives only or unless the alternatives are mutually exclusive, although the disclosure supports a definition that refers only to alternatives and "and/or." Throughout this application, the term "about" is used to indicate that a value includes the inherent variation of error for the device, the method being employed to determine the value or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Unless otherwise specified, the term "alkyl" used herein refers to a straight or branched hydrocarbon group containing 1 to 30 carbon atoms, preferably 1 to 20 carbon atoms, and most preferably 1 to 12 carbon atoms, such as methyl, ethyl, isopropyl, tert-butyl, and the like; or a cyclic saturated hydrocarbon group having 3 to 20 carbon atoms, and preferably 3 to 10 carbon atoms, such as cyclopropyl, cyclopentyl, cyclohexyl, menthyl, and the like.

Unless otherwise specified, the term "alkynyl" used herein refers to a straight or branched hydrocarbon group containing 2 to 30 carbon atoms, and preferably 3 to 20 carbon atoms and one or more carbon-to-carbon triple bonds such as pentynyl, propynyl, and the like; or a cyclic unsaturated hydrocarbon group having 6 to 20 carbon atoms and one or more carbon-to-carbon triple bonds.

Unless otherwise specified, the term "aryl" used herein refers to a monocyclic or polycyclic aromatic hydrocarbon radical, and having 6 to 30 carbon atoms, and preferably 6 to 20 carbon atoms, such as phenyl, naphthyl, anthryl, phenanthryl and the like.

Unless otherwise specified, the term "aralkyl" used herein refers a straight or branched hydrocarbon containing 1 to 20 carbon atoms and one or more aryl group as described above, such as benzyl, benzhydryl, fluorenylmethyl, and the like.

Each of the above mentioned alkyl, alkynyl, aryl, and aralkyl may optionally be substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, and carbonyl, or a heterocyclic group selected from the group consisting of pyridinyl, thiophenyl, furanyl, imidazolyl, morpholinyl, oxazolinyl, piperidinyl, piperazinyl, tetrahydropyranyl, pyrrolidinyl, pyrrolidinonyl, and the like.

Unless otherwise specified, the term "protective groups for the hydroxyl groups" has the meaning conventionally defined in organic synthetic chemistry, i.e., a group capable of protecting a hydroxyl group or moiety of a compound against the attacks of a chemical reaction.

Examples of the protective groups for the hydroxyl groups include, but are not limited to, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, I-ethoxyethyl, I-methyl-1-methoxyethyl, triphenylmethyl, allyl, benzyl, substituted benzyl, and $SiR_aR_bR_c$ wherein $R_a$, $R_b$ and $R_c$ are each independently unsubstituted or substituted alkyl or unsubstituted or substituted aryl, such as $C_{1-4}$ alkyl, phenyl, benzyl, substituted phenyl, and substituted benzyl.

In the depiction of the compounds given throughout this description, an unwedged bold bond ( ▬▬▬ ) or a wedged bold bond ( ▬▬ ) means a bond projecting above the plane of the paper. An unwedged hashed bond ( ⁞⁞⁞⁞⁞ ) or a wedged hashed bond ( ⁞⁞⁞⁞ ) means a bond projecting below the plane of the paper. A wedged bold bond ( ▬▬ ) and a wedged hashed bond ( ⁞⁞⁞⁞ ) are used for absolute configuration; an unwedged bold bond ( ▬▬▬ ) and an unwedged hashed bond ( ⁞⁞⁞⁞⁞ ) represent relative configuration and racemic character; and a wavy bond ( ∿∿∿ ) means a bond projecting almost half above and half below the plane of the paper.

Synthetic Route of Racemic Cyclopentenone of Formula 1'

The present invention provides a preparation process of a racemic cyclopentenone of Formula 1':

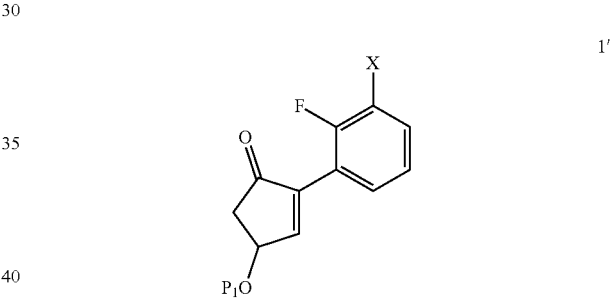

wherein $P_1$ is a protective group for hydroxyl groups, and X is Cl, Br, I, or —$CH_2CH_2CH_2COOR_1$, wherein $R_1$ is $C_{1-7}$-alkyl or $C_{7-11}$-aralkyl.

According to the invention, the compound of Formula 1' can be prepared according to the reactions shown in Scheme B. As shown in Scheme B, a compound of Formula 5, wherein X is Cl, Br, or I, reacts with lithium diisopropylamide (LDA) to convert it into an organolithium intermediate via regioselective lithiation, followed by formylation with dimethylformamide (DMF) to obtain a compound of Formula 6, wherein X is as defined above (Step 1). Then, the compound of Formula 6 is treated with 2-lithiofuran via 1,2-addition reaction to provide a compound of Formula 7 (Step 2). Thereafter, the compound of Formula 7 undergoes a Piancatelli rearrangement (Step 3) and isomerization (Step 4) to afford a cyclopentenone of Formula 1". Finally, the secondary hydroxyl group of the compound of Formula 1" is protected to obtain a compound of Formula 1', wherein $P_1$ is a protective group for hydroxyl groups, and X is as defined above (Step 5). In some embodiments, a Suzuki cross-coupling reaction can be performed to the compound of Formula 6, 7, 8, 1", or 1', wherein X is Cl, Br, or I, to form a compound of Formula 6, 7, 8, 1", or 1', wherein X is —$CH_2CH_2CH_2COOR_1$, and wherein $R_1$ is $C_{1-7}$-alkyl or $C_{7-11}$-aralkyl,

Scheme B

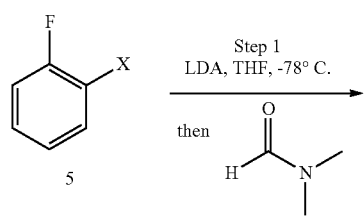

Step 1
LDA, THF, -78° C.
then

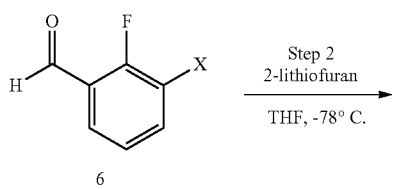

Step 2
2-lithiofuran
THF, -78° C.

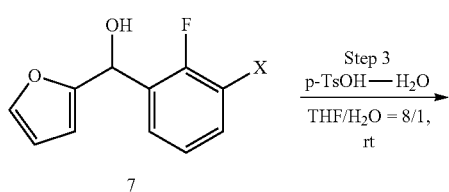

Step 3
p-TsOH—H₂O
THF/H₂O = 8/1,
rt

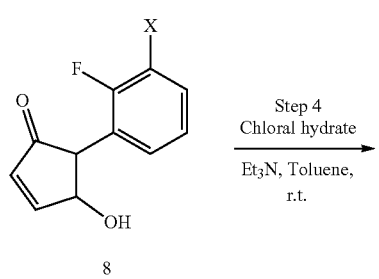

Step 4
Chloral hydrate
Et₃N, Toluene,
r.t.

[Structure 1″]

Step 5

-continued

[Structure 1′]

The present invention also provides a racemic or optically enriched compound of Formula 1:

[Structure 1]

wherein P is H or $P_1$; X is Cl, Br, I, or —$CH_2CH_2CH_2COOR_1$, wherein $R_1$ is $C_{1-7}$-alkyl or $C_{7-11}$-aralkyl; and $P_1$ is a protective group for the hydroxyl groups.

Chiral Resolution of Racemic Cyclopentenone of Formula 1″

According to the invention, the racemic cyclopentenone of Formula 1″ can be chirally resolved easily to form a cyclopentenone enriched in (R)-enantiomer and having high optical purity according to the reactions shown in Scheme C. As shown in Scheme C, the racemic compound of Formula 1″, wherein X is Cl, Br or I, is resolved via enantioselective esterification by using a first lipase to form a mixture of unreacted alcohol of Formula (S)-1″ and an ester of Formula 8 (Step 1). Then, the unreacted alcohol of Formula (S)-1″ can be easily removed, e.g., by isolating it from the mixture via column purification, and then proceeding to undergo a Mitsunobu reaction to afford the corresponding compound of Formula 8. Alternatively, the mixture can directly undergo a Mitsunobu reaction (Step 2) to convert the unreacted alcohol of Formula (S)-1″ into the compound of Formula 8. Finally, the compound of Formula 8 is deacylated to form a compound of Formula (R)-1″ enriched in (R)-enantiomer and having high optical purity by using a chemical hydrolysis reaction or an enzymatic cleavage reaction, Scheme C

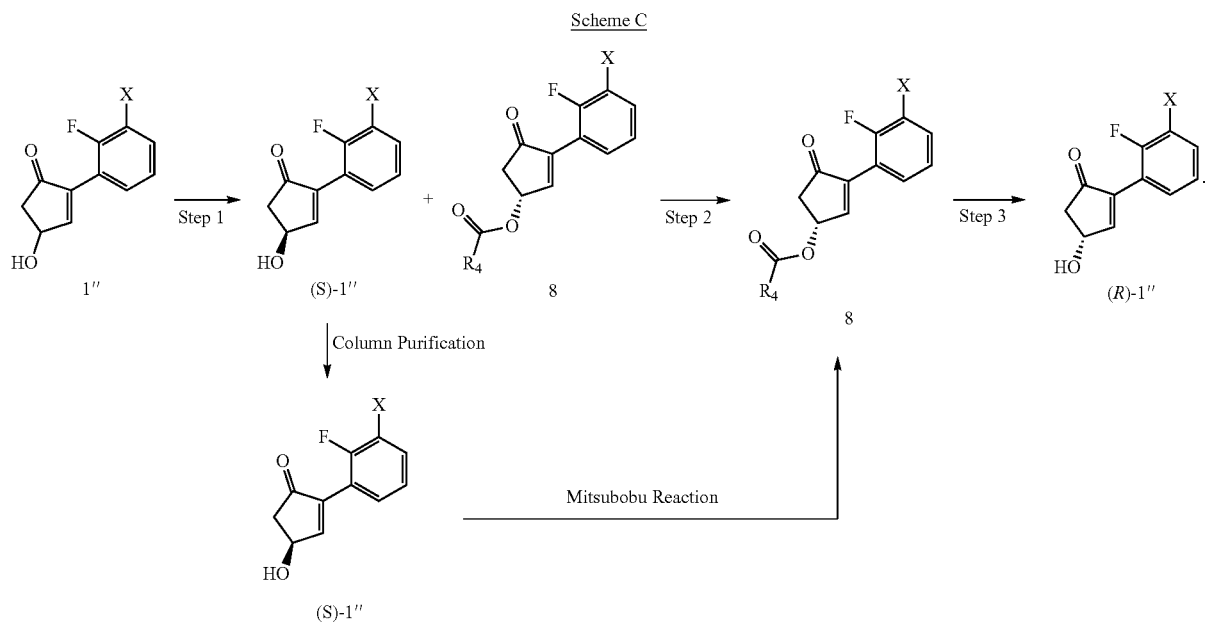

In Step 1 of Scheme C, the enantioselective esterification of the cyclopentenone of Formula 1" is performed with an acyl donor of Formula D, wherein $R_4$ and $R_5$ are independently H or $C_{1-6}$ alkyl, in the presence of a first lipase, wherein the acyl donor preferentially reacts with the cyclopentenone in (R) form, thereby generating a mixture essentially consisting of an optically active ester of Formula 8 and an unreacted alcohol of Formula (S)-1",

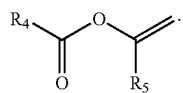

D

In some embodiments, a suitable first lipase is commercially available and can be derived from *Achromobacter* sp., *Candida cylindracea*, *Alcaligenes* sp., *Candida antarcitica*, *Pseudomonas cepacia*, *Burkholderia cepacian*, *Pseudomonas stutzri*, or a mixture thereof, preferably *Alcaligenes* sp., *Candida cylindracea*, *Candida antarcitica*, *Burkholderia cepacia* or *Pseudomonas stutzri*, and most preferably *Burkholderia cepacia*. A suitable acyl donor includes, but is not limited to, vinyl acetate, isopropenyl acetate, vinyl valerate, isopropenyl valerate, vinyl butyrate, isopropenyl butyrate, and a mixture thereof, and vinyl acetate is particularly preferable. Furthermore, the enantioselective esterification reaction may be performed in a single organic solvent or a mixture of organic solvents, such as hexane, cyclohexane, toluene, tetrahydrofuran, methyl ethyl ketone, methyl isobutyl ketone, ether, isopropyl ether, methyl isopropyl ether, tert-butyl methyl ether, and a mixture thereof. An appropriate reaction temperature ranges from about 5° C. to about 50° C., preferably at ambient temperature.

Step 2 of Scheme C pertains to a Mitsunobu reaction. The unreacted alcohol of Formula (S)-1" can be easily separated from the mixture obtained from Step 1 of Scheme C by column purification due to the different polarity of alcohol and ester to undergo a Mitsunobu reaction for forming the ester of Formula 8. In some embodiments, it is not necessary to separate the compounds of Formula (S)-1" and Formula 8 from the mixture, and the mixture can directly undergo a Mitsunobu reaction to convert the unreacted alcohol of Formula (S)-1" into the ester of Formula 8. In this step, almost 100% of the alcohol of Formula (S)-1" in the mixture can be converted into the ester of Formula 8.

In the Mitsunobu reaction, the unreacted alcohol of Formula (S)-1" can be treated with an acyloxy donor of Formula $R_4COOH$ (wherein $R_4$ is H or $C_{1-6}$ alkyl), to convert it into the compound of Formula 8 in the presence of dialkyl azodicarboxylate and trialkyl/triaryl phosphine in a suitable solvent. A suitable dialkyl azodicarboxylate includes, but is not limited to, dimethyl azodicarboxylate (DMAD), diethyl azodicarboxylate (DEAD), diisopropyl azodicarboxylate (DIAD), di-tert-butyl azodicarboxylate (DTBAD), dibenzyl azodicarboxylate (DBAD), bis-trichloroethyl azodicarboxylate (BTCEAD), di-p-chlorobenzyl azodicarboxylate (DCAD), di-4-nitrobenzyl azodicarboxylate (DNAD), dicyclopentyl azodicarboxylate (DCpAD), and a mixture thereof; and preferably diethyl azodicarboxylate, diisopropyl azodicarboxylate, dibenzyl azodicarboxylate, and a mixture thereof. A suitable trialkyl/triaryl-phosphine includes, but is not limited to, tri-n-butyl phosphine, triphenylphosphine, and a mixture thereof; and preferably triphenylphosphine. A suitable solvent in the Mitsunobu reaction includes, but is not limited to, tetrahydrofuran, toluene, benzene, dimethylformamide, diethyl ether, acetonitrile, dichloromethane, and a mixture thereof. The Mitsunobu reaction is preferably carried out at an appropriate temperature ranging from about −30° C. to about 70° C., preferably at ambient temperature.

Step 3 of Scheme C pertains to a deacylation reaction, such as a chemical hydrolysis reaction or an enzymatic cleavage reaction. In some embodiments, the deacylation reaction is a chemical hydrolysis reaction using an acid catalyst in an alcohol system. A suitable acid catalyst includes, but is not limited to, phosphoric acid, p-toluenesulfonic acid, hydrobromic acid, hydrochloric acid, nitric acid, sulfuric acid, and a mixture thereof. A suitable alcohol in the alcohol system includes, but is not limited to, methanol, ethanol, propanol, isopropanol, butanol, isobutanol, and a mixture thereof. For example, the chemical hydrolysis reaction of the compound of Formula 8 is performed in the presence of sulfuric acid and methanol.

In some embodiments, the deacylation reaction in Step 3 of Scheme C is an enzymatic cleavage reaction. The enzymatic cleavage reaction can be performed in the presence of a second lipase in a suitable organic solvent or an aqueous system at an appropriate temperature to obtain the compound of Formula (R)-1". A suitable second lipase is commercially available and can be derived from *Achromobacter* sp., *Alcaligenes* sp., *Candida antarcitica*, *Pseudomonas cepacia*, *Pseudomonas stutzri*, *Pseudomonas* sp., or a mixture thereof, and preferably from *Achromobacter* sp., *Alcaligenes* sp., *Candida antarcitica*, *Pseudomonas* sp., or a mixture thereof; and most preferably from *Candida antarcitica*.

According to the invention, the deacylation reaction is monitored for the purpose of an optical purity of the resultant compound of Formula (R)-1". In some embodiments, the deacylation is monitored by HPLC using a chiral column and stopped by removing the second lipase, preferably when the optical purity of the resultant compound decreases to about 95% e.e., preferably about 99% e.e., and more preferably about 99.9% e.e. In some embodiments, the unreacted ester of Formula 8 and it's enantiomer can be removed such as by column chromatography after the deacylation reaction. According to the invention, the compound of Formula (R)-1" is produced with an optical activity of at least about 95% e.e., preferably at least about 99% e.e., and most preferably at least about 99.9% e.e.

Accordingly, the present invention provides a process for preparing a compound of Formula (R)-1" enriched in (R)-enantiomer and having an optical purity of at least 95% e.e.,

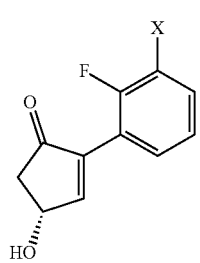

(R)-1"

wherein X is Cl, Br, or I, the process comprising the steps of:
(1) enantioselectively (R)-esterifying a compound of Formula 1":

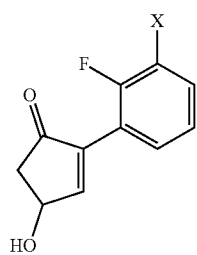

1"

with an acyl donor of Formula D:

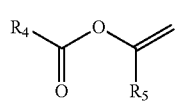

D wherein $R_4$ and $R_5$ are independently H or $C_{1-6}$ alkyl, and a first lipase, to form a mixture of (S)-alcohol and (R)-ester:

(2) optionally removing the (S)-alcohol; and
(3) deacylation the (R)-ester.

In some embodiments, a Suzuki cross-coupling reaction can be performed to the compound of Formula (R)-1", wherein X is Cl, Br, or I, to form a compound of Formula (R)-1", wherein X is —$CH_2CH_2CH_2COOR_1$, and wherein $R_1$ is $C_{1-7}$-alkyl or $C_{7-11}$-aralkyl.

Preparation of Benzoprosacyclin Analogue of Formula 4

The present invention also provides a preparation process of a benzoprostacyclin analogue of Formula 4:

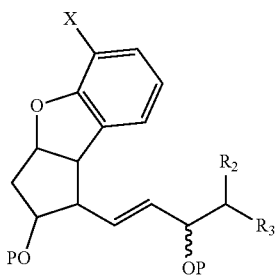

4 wherein P is H, $P_1$ or $P_2$; $R_2$ is H or $C_{1-4}$-alkyl; $R_3$ is $C_{1-7}$-alkyl. $C_{2-7}$-alkynyl, aryl, or aryloxy, each of which is unsubstituted or substituted by $C_{1-4}$-alkyl, halogen, or trihalomethyl; X is Cl, Br, I, or —$CH_2CH_2CH_2COOR_1$, wherein $R_1$ is $C_{1-7}$-alkyl or $C_{7-11}$-aralkyl; and $P_1$ and $P_2$ are protective groups for the hydroxyl groups.

According to the invention, the compound of Formula 4 can be prepared according to the reactions shown in Scheme D. As shown in Scheme D, the synthesis of the compound of Formula 4 starts from the compound of Formula 1', wherein Step 1 pertains to a 1,4-addition reaction, Step 2 pertains to a reduction reaction, and Step 3 pertains to an intramolecular cyclization reaction, Scheme D

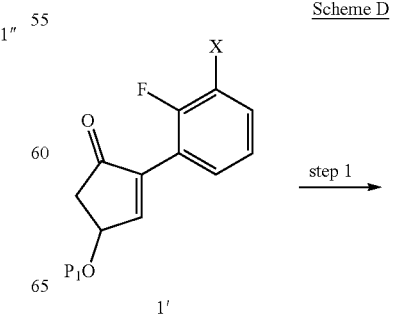

1'

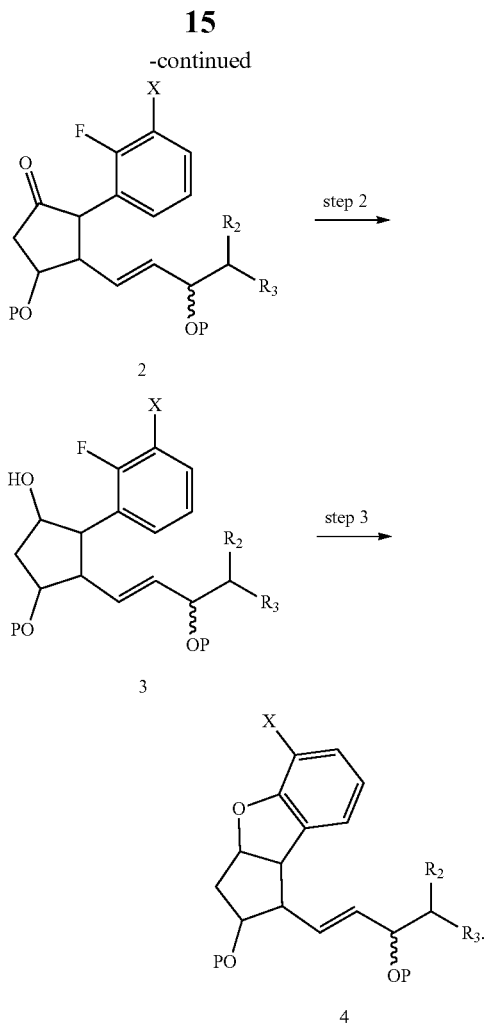

The subsequently described details can be used for any of the processes for the preparation of the benzoprostacyclin analogues of the present invention. In Step 1 of Scheme D, a cyclopentenone of Formula 2, wherein P, X, $R_2$ and $R_3$ are as defined above, is prepared by coupling reaction of the cyclopentenone of Formula 1', wherein $P_1$ and X are as defined above, with a m-side chain unit of a cuprate derived from a compound of Formula $L_1$, Formula $L_2$ or Formula $L_3$, wherein Y is Cl, Br, or I; $P_2$, $R_2$ and $R_3$ are as defined above. In some embodiments, the reaction is performed at a temperature ranging from about −100° C. to about −20° C., preferably at about −80° C. to about −40° C., Step 2 of Scheme D involves a keto-reduction reaction. In Step 2, the C9-carbonyl group of the compound of Formula 2 is reduced to a α-hydroxyl group with a reducing reagent. A suitable reducing reagent includes, but is not limited to, sodium bis(2-methoxyethoxy)aluminum hydride, diisobutylaluminum hydride, lithium tri-tert-butoxyaluminohydride, lithium tri-alkyl borohydride, potassium tri-alkyl borohydride, sodium tri-alkyl borohydride, and a mixture thereof; preferably lithium tri-sec-butylborohydride (L-selectride), sodium tri-sec-butylborohydride (N-selectride), potassium tri-sec-butylborohydride (K-selectride), lithium tri-amylborohydride, potassium tri-amylborohydride, and a mixture thereof; and lithium tri-sec-butylborohydride (L-selectride) is more preferable in this step as a reducing reagent.

As shown in Step 3 of Scheme D, a benzoprostacyclin analogue of Formula 4 is prepared by an intramolecular cyclization reaction of the compound of Formula 3 in the presence of a suitable base condition. In some embodiments, the intramolecular cyclization reaction is achieved by using a suitable base in a suitable solvent at a temperature ranging from about 0° C. to about 120° C. A suitable base includes, but is not limited to, sodium hydride, potassium hydride, lithium hydride, potassium tert-butoxide, butyllithium, and a mixture thereof. A suitable solvent includes, but is not limited to, tetrahydrofuran, 2-methyl tetrahydrofuran, glyme, dimethylformamide, N,N'-dimethylpropyleneurea, 1,2-dimethoxypropane, toluene, and a mixture thereof.

In comparison with the conventional conjugate addition reaction shown in Scheme A which requires five (5) steps to form the tricyclic structure of benzoprostacyclin, the process of the present invention only requires three (3) steps to form the tricyclic structure of benzoprostacyclin. The process of the present invention is a more efficient conjugate addition approach.

In some embodiments, the obtained compound of Formula 2, 3, or 4 can be subjected to a deprotection reaction to remove the protecting groups for the hydroxyl groups.

In some embodiments, a Suzuki cross-coupling reaction can be performed to the compound of Formula 2, 3, or 4, wherein X is Cl, Br or I, to form a compound of Formula 2, 3, or 4, wherein X is —$CH_2CH_2CH_2COOR_1$, and wherein $R_1$ is $C_{1-7}$-alkyl or $C_{7-11}$ aralkyl. The Suzuki cross-coupling reaction is preferably carried out in the presence of an alkyl borane of Formula $BR_2$—$CH_2CH_2CH_2COOR_1$, wherein R is an alkyl group, which is prepared from an alkyl ($R_1$) 3-butenoate, wherein $R_1$ is $C_{1-7}$-alkyl or $C_{7-11}$-aralkyl, with a borane reagent such as 9-borabicyclo[3.3.1]nonane (9-BBN), disiamylborane, diisoamylborane, catecholborane, diisopinocamphenylborane, dicyclohexylborane, bis(pinacolato)diboron, and a mixture thereof. The Suzuki cross-coupling reaction can also be carried out in the presence of a palladium catalyst, a ligand, and a base at a temperature ranging from about 50° C. to about 60° C. under nitrogen or argon. A suitable palladium catalyst includes, but is not limited to, $Pd(PPh_3)_4$, $Pd(dppf)_2Cl_2$-DCM, $Pd(dppf)_2Cl_2$, $Pd(OAc)_2$, $Pd_2(dba)_3$, bis(eta3-allyl-mu-chloropalladium(II)), and a mixture thereof. In some embodiments, the palladium catalyst can be treated with a ligand to form palladium complexes for promote the reactivity of the cross-coupling reaction. A suitable ligand includes, but is not limited to, $PPh_3$, $AsPh_3$, $P(OMe)_3$, $(n-Bu)_3P$, dppe, dppp, dicyclohexyl-(2,6-dimethoxy biphenyl-2yl)phosphane, and a mixture thereof. A suitable base can increase the reactivity of the alkyl borane toward forming a Pd-halide complex to promote the cross-coupling rate, which includes, but is not limited to $Li_2CO_3$, $Na_2CO_3$, $K_2CO_3$, $Cs_2CO_3$, NaOMe, $K_3PO_4$, t-BuONa, t-BuOK, $K_3PO_4$, NaOH, and a mixture thereof. In some embodiments, the Suzuki cross-coupling reaction is performed in the presence of $Pd(dppf)_2Cl_2$-DCM, $AsPh_3$, and $K_3PO_4$ at 60° C. in tetrahydrofuran solvent.

Accordingly, the present invention provides a process for preparing a compound of Formula 4:

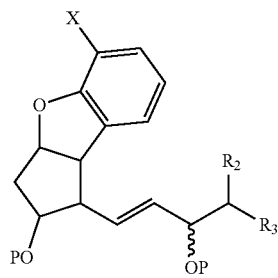
4 wherein P is H, $P_1$ or $P_2$; $R_2$ is H or $C_{1-4}$-alkyl; $R_3$ is $C_{1-7}$-alkyl, $C_{2-7}$-alkynyl, aryl, or aryloxy, each of which is unsubstituted or substituted by $C_{1-4}$-alkyl, halogen, or trihalomethyl; X is Cl, Br, I, or $—CH_2CH_2CH_2COOR_1$, wherein $R_1$ is $C_{1-7}$-alkyl or $C_{7-11}$-aralkyl; and $P_1$ and $P_2$ are protective groups for the hydroxyl groups, the process comprising the steps of:

(1) reacting a compound of Formula 1':

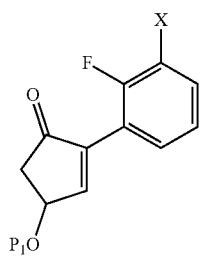
1' wherein $P_1$ and X are as defined above, with a cuprate derived from a compound of Formula $L_1$, Formula $L_2$, or Formula $L_3$:

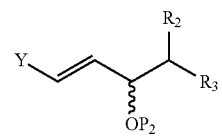
$L_1$

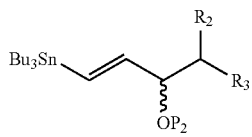
$L_2$

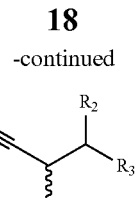
$L_3$ wherein Y is Cl, Br, or I; $P_2$, $R_2$ and $R_3$ are as defined above, to form a compound of Formula 2:

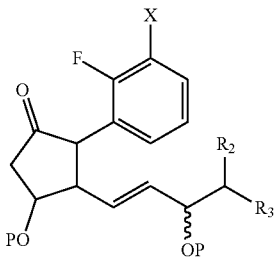
2 wherein P, X, $R_2$ and $R_3$ are as defined above;

(2) reducing a ketone of the compound of Formula 2 to form a compound of Formula 3:

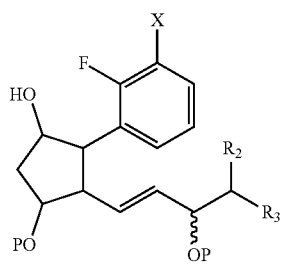
3 wherein P, X, $R_2$ and $R_3$ are as defined above;

(3) performing an intramolecular cyclization reaction of the compound of Formula 3 to form a compound of Formula 4:

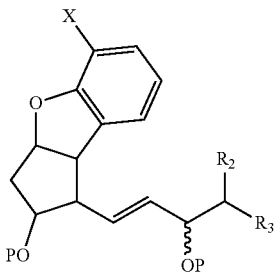
4 wherein P, X, $R_2$ and $R_3$ are as defined above;

(4) optionally performing a deprotecting reaction to remove the protective groups for the hydroxyl groups; and (5) optionally performing a Suzuki cross-coupling reaction of the compound of Formula 2, 3 or 4 wherein X is Cl, Br or I, to form the compound of Formula 2, 3 or 4 wherein X is —CH$_2$CH$_2$CH$_2$COOR$_1$ and R$_1$ is as defined above.

Synthetic Route of Optically Enriched Benzoprostacyclin Analogue of Formula 4a

The present invention further provides a preparation process of an optically enriched compound of Formula 4a:

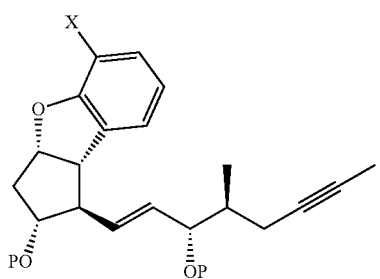

4a wherein P is H, P$_1$ or P$_2$; X is Cl, Br, I, or —CH$_2$CH$_2$CH$_2$COOR$_1$, wherein R$_1$ is C$_{1-7}$-alkyl or C$_{7-11}$-aralkyl; and P$_1$ and P$_2$ are protective groups for the hydroxyl groups.

As depicted in Scheme E, the synthesis of the compound of Formula 4a is similar to that of Formula 4 as shown in Scheme D. The synthesis of the compound of Formula 4a starts from an optically enriched compound of Formula (R)-1', wherein P$_1$ and X are as defined above, and an optically enriched compound of Formula L$_{1a}$, Formula L$_{2a}$ or Formula L$_{3a}$,

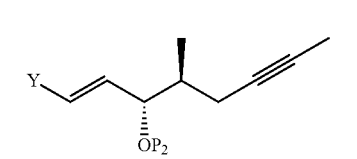

L$_{1a}$

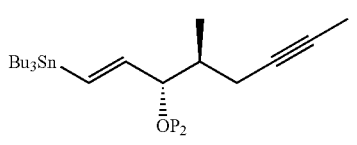

L$_{2a}$

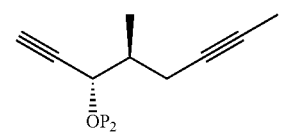

L$_{3a}$ wherein Y is Cl, Br, or I; and P$_2$ is a protective group for the hydroxyl groups,

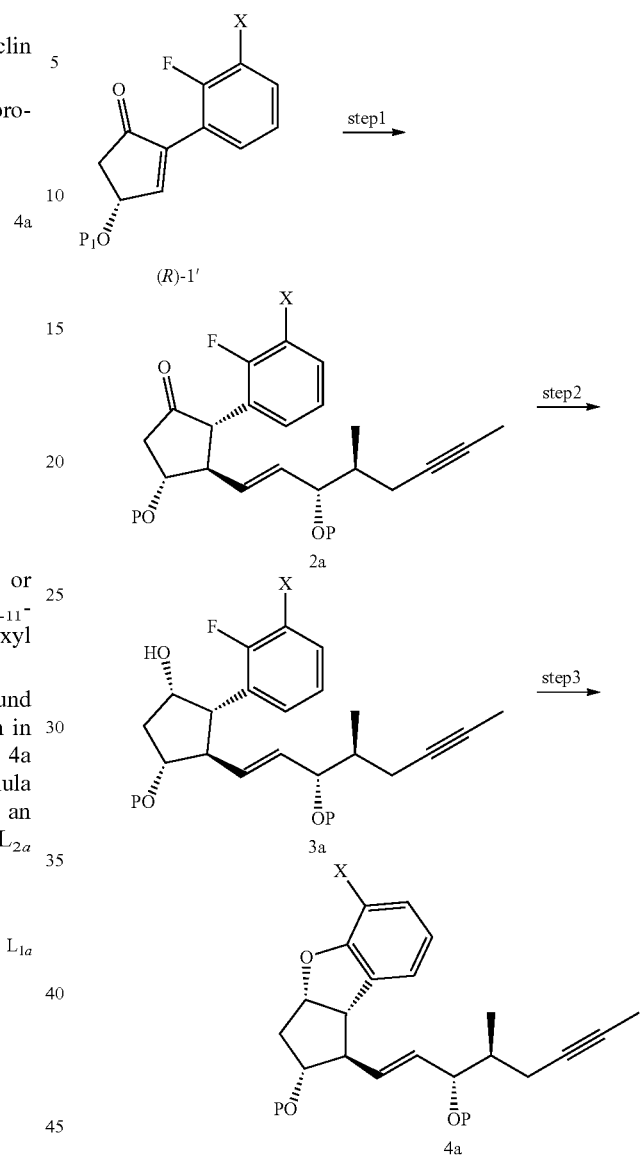

Scheme E

In Step 1 of Scheme E, a compound of Formula 2a is prepared by a coupling reaction of the optically enriched compound of Formula (R)-1' with a ω-side chain unit of a cuprate derived from an optically enriched compound of Formula L$_{1a}$, L$_{2a}$ or L$_{3a}$. Then, the compound of Formula 2a, is subjected to a reduction reaction (Step 2) and an intramolecular cyclization (Step 3) to obtain the compound of Formula 4a, wherein X and P are as defined above.

In some embodiments, the obtained compound of Formula 2a, 3a, or 4a can be subjected to a deprotection reaction to remove the protecting groups for the hydroxyl groups.

In some embodiments, the compound of Formula 2a, 3a or 4a, wherein X is Cl, Br, or I, can be converted to the compound of Formula 2a, 3a or 4a, wherein X is —CH$_2$CH$_2$Cl$_2$COOR$_1$, wherein R$_1$ is C$_{1-7}$-alkyl or C$_{7-11}$-aralkyl, via a Suzuki cross-coupling reaction.

Accordingly, the present invention provides a process for preparing an optically enriched compound of Formula 4a,

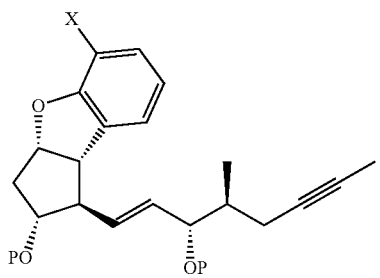

4a wherein P is H, P₁ or P₂; X is Cl, Br, I, or —CH₂CH₂CH₂COOR₁, wherein R₁ is $C_{1-7}$-alkyl or $C_{7-11}$-aralkyl; and P₁ and P₂ are protective groups for the hydroxyl groups;

the process comprising the steps of:
(1) reacting an optically enriched compound of Formula (R)-1':

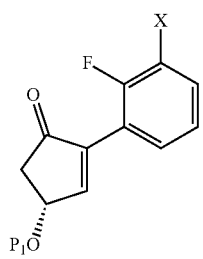

(R)-1' wherein P₁ and X are as defined above, with a cuprate derived from an optically enriched compound of Formula $L_{1a}$, Formula $L_{2a}$, or Formula $L_{3a}$:

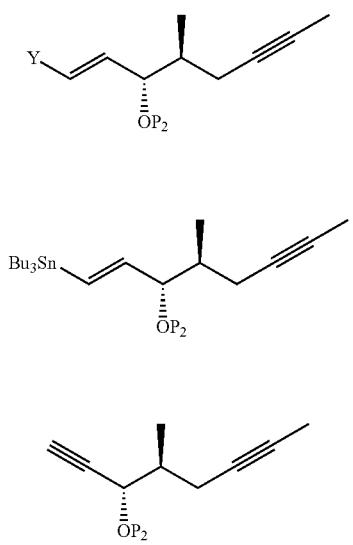

$L_{1a}$ $L_{2a}$ $L_{3a}$ wherein Y is Cl, Br, or I; and P₂ is a protective group for the hydroxyl groups, to form a compound of Formula 2a:

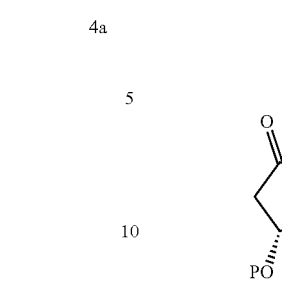

2a wherein P and X are as defined above;

(2) reducing a ketone of the compound of Formula 2a to form a compound of Formula 3a:

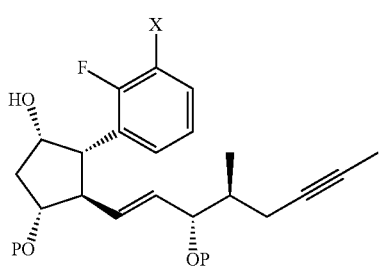

3a wherein P and X are as defined above;

(3) performing an intramolecular cyclization of the compound of Formula 3a to form the compound of Formula 4a:

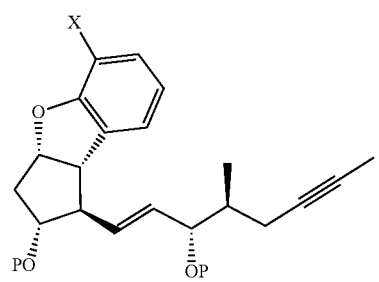

4a wherein P and X are as defined above;

(4) optionally performing a deprotecting reaction to remove the protective groups for the hydroxyl groups; and (5) optionally performing a Suzuki cross-coupling reaction of the compound of Formula 2a, 3a or 4a when X is Cl, Br, or I, to form the compound of Formula 2a, 3a or 4a wherein X is —CH₂CH₂CH₂COOR₁ and R₁ is as defined above.

Synthetic Route of Benzoprostacyclin Analogue of Formula 4b

The present invention further provides a preparation process of the compound of Formula 4b,

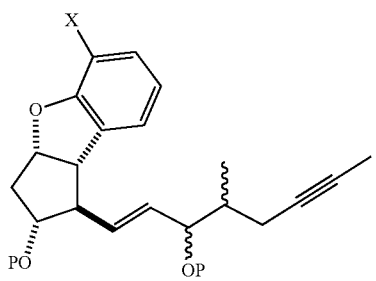

wherein P is H, P₁ or P₂; X is Cl, Br, I, or —CH$_2$CH$_2$CH$_2$COOR$_1$, wherein R$_1$ is C$_{1-7}$-alkyl or C$_{7-11}$-aralkyl; and P$_1$ and P$_2$ are protective groups for the hydroxyl groups.

The compound of Formula 4b can be prepared according to the reactions shown in Scheme F:

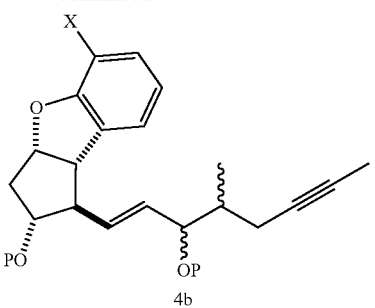

The synthetic route of the compound of Formula 4b shown in Scheme F is also similar to the reactions depicted in Scheme D or E. In Step 1 of Scheme F, the racemic cyclopentenone of Formula 1' reacts with a cuprate formed from a racemic and diastereomeric mixture comprising a compound of Formula L$_{1b}$, Formula L$_{2b}$ or Formula L$_{3b}$,

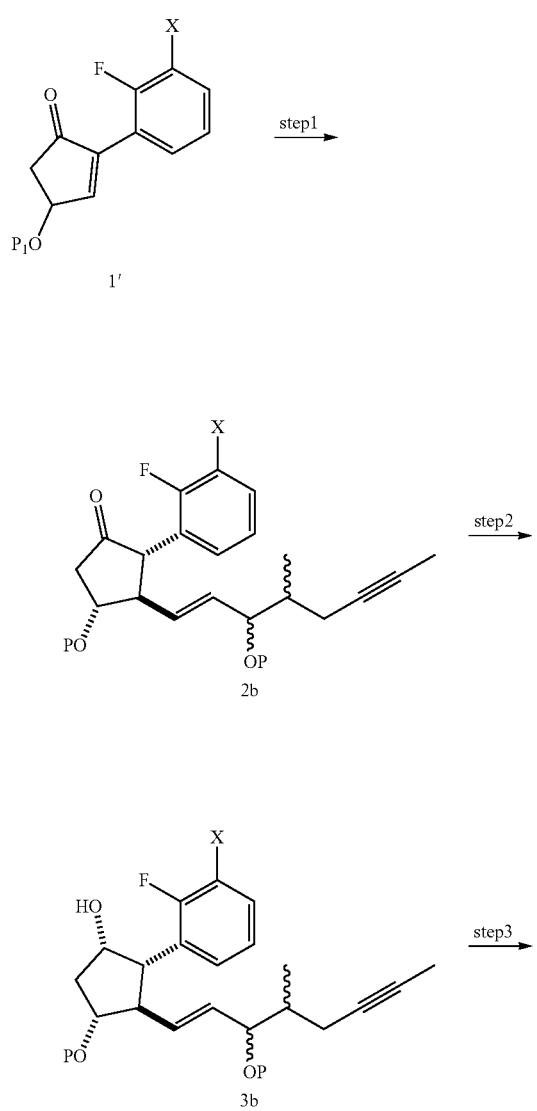

wherein Y is Cl, Br, or I, and P$_2$ is as defined above, via a coupling reaction to form a compound of Formula 2b (Step 1). Thereafter, the compound of Formula 2b is subjected to a reduction reaction (Step 2) and an intramolecular cyclization reaction (Step 3) to form a mixture or composition comprising a compound of Formula 4b, a compound of Formula 11,15-Syn 4b, and a compound of Formula 11,15-Anti 4b, wherein P and X are as defined above),

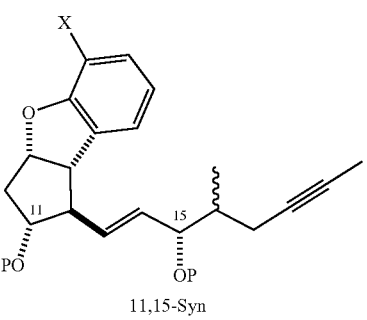

-continued

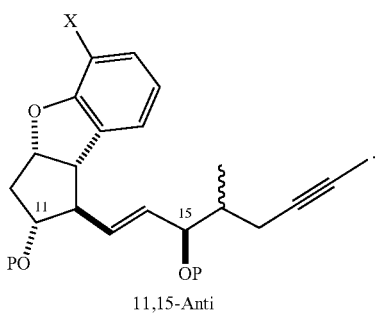

11,15-Anti

In general, the undesired 11,15-Anti isomer of the compound of Formula 4b could be obtained in an amount of about 50% by the treatment of the racemic cyclopentenone of Formula 1' with the racemic cuprate.

However, there is an unexpected result that the coupling reaction of the present invention has high selectivity to form the 11,15-Syn isomer of the compound of Formula 4b, and thus the ratio of the compound of Formula 11,15-Syn 4b and the compound of Formula 11,15-Anti 4b is observed about 70% or more- and about 30% or less, as detected by HPLC. The unexpected result shows that 11(R)-enantiomer of the racemic cyclopentenone 1' and 15(S)-enantiomer of the racemic cuprate, or 11(S)-enantiomer of the racemic cyclopentenone 1' and 15(R)-enantiomer of the racemic cuprate is a matched pair, so the coupling reaction thereof tends to form 11,15-Syn isomer. In contrast, 11(R)-enantiomer of the racemic cyclopentenone 1' and 15(R)-enantiomer of the racemic cuprate, or 11(S)-enantiomer of the racemic cyclopentenone 1' and 15(S)-enantiomer of the racemic cuprate is a mismatched pair, so the coupling reaction thereof does not tend to generate, 11,15-Anti isomer. According to the invention, the undesired 11,15-Ami isomer (also called 15-epimer) can be separated by column chromatography or crystallization.

In some embodiments, the compound of Formula 2b, 3b, or 4b, wherein P is H, can be obtained by deprotection of the protecting groups of the compound of Formula 2b, 3b, or 4b wherein P is a protective group for the hydroxyl groups.

In some embodiments, the compound of Formula 2b, 3b or 4b, wherein X is Cl, Br, or I, can be converted to a compound of Formula 2b, 3b or 4b, wherein X is —CH$_2$CH$_2$CH$_2$COOR$_1$, wherein R$_1$ is C$_{1-7}$-alkyl or C$_{7-11}$-aralkyl, via a Suzuki cross-coupling reaction.

Accordingly, the present invention provides a process for preparing a racemic compound of Formula 4b:

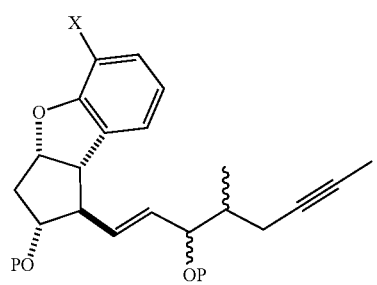

4b wherein P is H, P$_1$ or P$_2$; X is Cl, Br, I, or —CH$_2$CH$_2$CH$_2$COOR$_1$, wherein R$_1$ is C$_{1-7}$-alkyl or C$_{7-11}$-aralkyl; and P$_1$ and P$_2$ are protective groups for the hydroxyl groups, the process comprising the steps of:

(1) reacting a racemic compound of Formula 1':

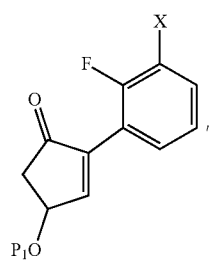

1 wherein P$_1$ and X are as defined above, with a cuprate derived from a racemic and diastereomeric mixture comprising a compound of Formula L$_{1b}$, Formula L$_{2b}$, or Formula L$_{3b}$:

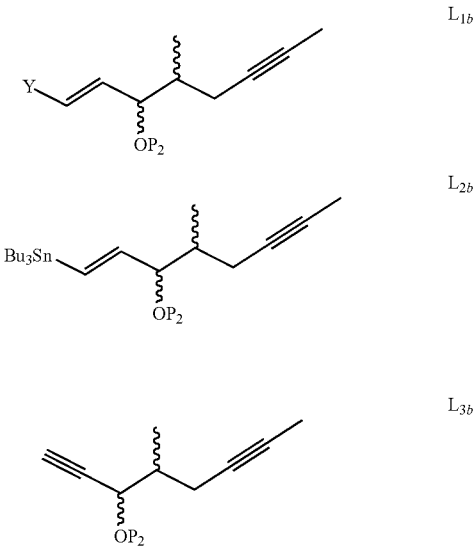

wherein Y is Cl, Br, or I; P$_2$ is as defined above, to form a compound of Formula 2b:

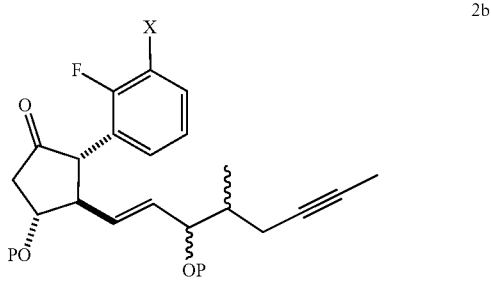

2b wherein P and X are as defined above:

(2) reducing a ketone of the compound of Formula 2b to form a compound of Formula 3b:

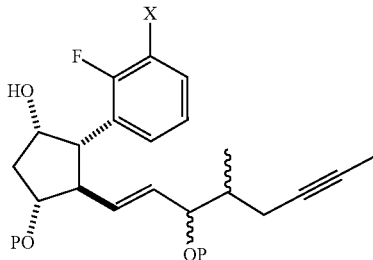

2b wherein P and X are as defined above;

(3) performing an intramolecular cyclization of the compound of Formula 3b to form the compound of Formula 4b:

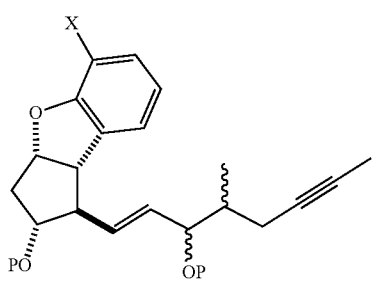

4b wherein P and X are as defined above;

(4) optionally performing a deprotecting reaction to remove the protective groups for the hydroxyl groups; and (5) optionally performing a Suzuki cross-coupling reaction of the compound of Formula 2b, 3b or 4b, wherein X is Cl, Br, or I, to form a compound of Formula 2b, 3b or 4b wherein X is —CH$_2$CH$_2$CH$_2$COOR$_1$ and R$_1$ is as defined above.

The present invention further provides a racemic intermediate of Formula 11,15-Syn 4b″, wherein Y is Cl, Br, or I, which is used for the preparation of Beraprost

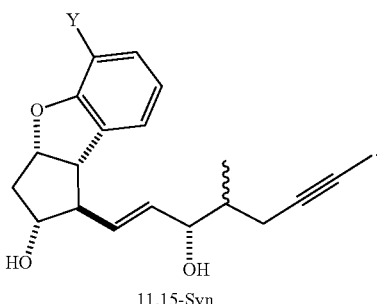

4b″

11,15-Syn

According to the invention, the racemic intermediate of Formula 11,15-Syn 4b″ at least comprises four 11,15-syn isomers of Formula 4b″-1, Formula 4b″-2, Formula 4b″-3, and Formula 4b″-4:

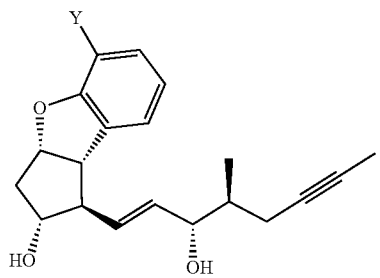

4b″-1

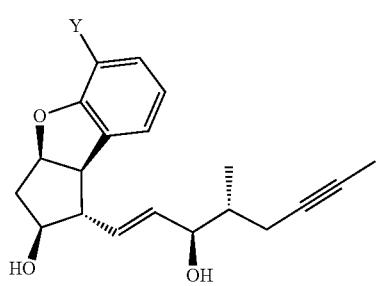

4b″-2

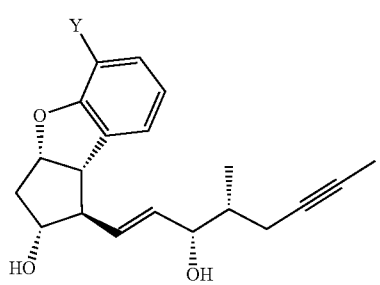

4b″-3

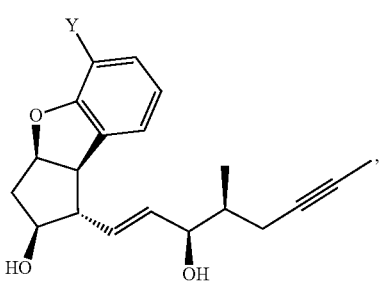

4b″-4 wherein Y is Cl, Br, or I.

The compounds of Formula 11,15-Syn 4b″ have excellent crystallinity, and thus can be easily purified by crystallization to remove the undesired 11,15-Anti isomers. Thus, the amount of the undesired 11,15-Anti isomer can be reduced to not more than about 5%, 1%, or 0.1% in the resultant intermediate mixture.

The present invention also provides a novel optically enriched intermediate of Formula 4a″, wherein Y is Cl, Br, or I, which is used for the preparation of Beraprost-314d,

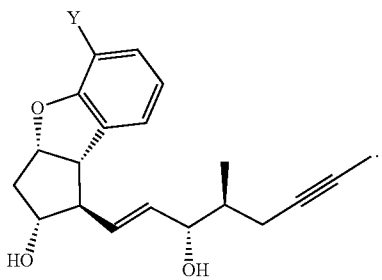

According to the invention, the compounds of Formula 4a" have excellent crystallinity, and thus can be easily crystallized by a crystallization process which is carried out from a polar/non-polar solvent mixture. A suitable polar/non-polar solvent system includes, but is not limited to, ethyl acetate/n-hexane, ethyl acetate/n-heptane, MTBE/n-heptane, and iPrOAc/n-heptane mixture. Furthermore, impurities generated from the preceding reactions could be reduced to not more than about 5%, 1%, or 0.1% by repeating crystallization processes to afford a high purity compound.

All of the compounds and/or processes disclosed and claimed herein can be made and executed without undue experimentation in light of the present disclosure. While the compounds and process of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutions and modifications apparent to those skilled in the art are deemed to be within the spirit, scope and concept of the invention as defined by the appended claims.

EXAMPLES

Example 1

(3-bromo-2-fluorophenyl)(furan-2-yl)methanol

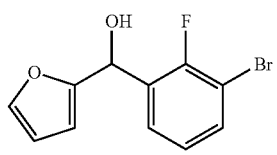 [SMILES: OC(c1ccco1)c1cccc(Br)c1F]

To a solution of diisopropylamine (43.3 g, 0.43 mole) in dry THF (220 mL) was added dropwise 1.6 M (270 mL 0.43 mole) n-BuLi in THF at −50° C. under nitrogen. The reaction mixture was allowed to warm up to −10° C. After one hour, the reaction mixture was cooled to −70° C. A solution of I-bromo-2-fluorobenzene (50.0 g, 0.29 mole) in dry THF (200 mL) was added slowly thereto by a dropping funnel, and the reaction temperature was kept between −70° C. and −65° C. Subsequently, the reaction mixture was stirred at −70° C. for 30 min. Then, a solution of furfural (28.8 g, 0.30 mole) in dry THF (29 mL) was added slowly thereto by a dropping funnel, and the reaction temperature was kept between −70° C. and −65° C. The completion of reaction was confirmed by TLC monitor. The reaction mixture was quenched with saturated aqueous ammonium chloride (400 mL). The reaction mixture was phase separated, and the aqueous layer was extracted with ethyl acetate (200 mL). The organic layers were combined and dried over anhydrous Na₂SO₄. The solid was filtered off and the organic solvent was evaporated off under vacuum to give 78 g of the crude title compound.

Example 2

5-(3-bromo-2-fluorophenyl)-4-hydroxycyclopent-2-enone

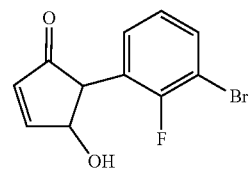 [SMILES: O=C1C=CC(O)C1c1cccc(Br)c1F]

The p-TsoH-H₂O (54.95 g, 0.29 mole) was added to a solution of (2-bromo-3-fluorophenyl)(furan-2-yl)methanol (78 g, 0.29 mole, from Example 1) in the mixture of THF/H₂O (780 mL, THF/H₂O=8/1), and the reaction mixture was stirred at 60° C. After the completion of reaction, the mixture was quenched by 10% aqueous NaH CO₃ (800 mL), and the reaction mixture was phase separated, and the aqueous layer was extracted with ethyl acetate (500 mL). The organic layers were combined and dried over anhydrous Na₂SO₄. The solid was filtered off and the organic solvent was evaporated off under vacuum to give 82.5 g of the crude title compound.

Example 3

2-(3-bromo-2-fluorophenyl)-4-hydroxycyclopent-2-enone

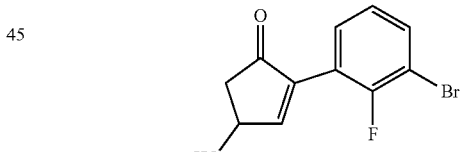

To a solution of crude 5-(3-bromo-2-fluorophenyl)-4-hydroxycyclopent-2-enone (82.5 g, from example 2) in toluene (825 mL) was added triethylamine (30.9 g, 0.305 mole) and chloral hydrate (5.05 g, 30.5 mmol) at room temperature. The completion of reaction was confirmed by TLC monitor. The mixture was washed by 10% NaCl$_{(aq)}$ (800 mL) and dried over anhydrous Na₂SO₄. The solid was filtered off and the organic solvent was evaporated off under vacuum. The crude product was purified by chromatography on silica gel using a mixture of hexane and ethyl acetate as a gradient eluent. Yield of the title compound was 28.81 g (45%, 3 steps).

¹H-NMR (400 MHz, CDCl₃): δ 7.813-7.824 (m, 1H), 7.716-7.756 (m, 1H), 7.512-7.552 (m, 1H), 7.036-7.079 (m, 1H), 5.099-5.114 (n, 1H), 2.931-2.993 (m, 1H), 2.455-2.507 (dd, 1H).

Example 4

2-(3-bromo-2-fluorophenyl)-4-((tetrahydro-2H-pyran-2-yl)oxy)cyclopent-2-enone

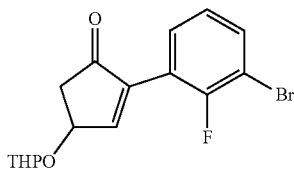

2-(3-bromo-2-fluorophenyl)-4-hydroxycyclopent-2-enone (51.0 g, 143.6 mmol, from Example 3) was dissolved with dichloromethane (510 mL). Then, acetic acid (740 mg, 9.4 mmol) and dihydropyridine (24 g, 285.3 mmol) were added thereto. The reaction mixture was stirred at room temperature. The completion of reaction was confirmed by TLC monitor. The reaction mixture was quenched with 10% NaHCO$_{3(aq)}$ (510 mL) and the reaction mixture was phase separated. The organic layer was collected and dried over anhydrous Na$_2$SO$_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 52 g (79%).

$^1$H-NMR (400 MHz, CDCl$_3$): δ 7.891-7.944 (d, 1H), 7.746-7.791 (m, 1H), 7.507-7.544 (t, 1H), 7.036-7.075 (t, 1H), 5.019-5.050 (m, 1H), 4.8174.884 (m, 1H), 3.870-3.960 (m, 1H), 3.549-3.604 (m, 1H), 2.875-2.985 (m, 1H), 2.489-2.667 (m, 1H), 1.539-1.862 (m, 6H)

Example 5

(R)-3-(3-bromo-2-fluorophenyl)-4-oxocyclopent-2-en-1-yl acetate

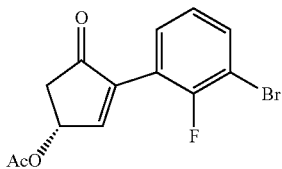

2-(3-bromo-2-fluorophenyl)-4-hydroxycyclopent-2-enone (25 g, 92.6 mmol, from Example 3) was diluted with toluene (250 mL), and then Lipase-SL (2.5 g) and vinyl acetate (25 g) were added thereto. The reaction mixture was stirred at room temperature for 2 hours. The completion of reaction was monitored by chiral HPLC column. The Lipase-SL was filtered from the reaction mixture, and the filtrate was concentrated to obtain the crude mixture (31.25 g)

Then, triphenylphosphine (15.18 g, 57.8 mmol) and acetic acid (3.47 g, 57.8 mmol) were added to the crude mixture in toluene (300 mL). The reaction mixture was stirred at room temperature until the triphenylphosphine was dissolved in reaction mixture. Then diisopropylazodicarboxylate was added slowly thereto. The completion of reaction was confirmed by TLC monitor. Further reaction solvent was removed under vacuum and the residue was suspended with the mixture of ethyl acetate (150 mL) and n-hexane (450 mL). The solid was filtered and the filtrate was evaporated under vacuum. The crude product was purified by chromatography on silica gel using a mixture of hexane and ethyl acetate as a gradient eluent. Yield of the title compound was 26.6 g (92%).

$^1$H-NMR (400 MHz, CDCl$_3$): δ 7.809-7.819 (m, 1H), 7.736-7.769 (m, 1H), 7.497-7.537 (m, 1H), 7.020-7.060 (m, 1H), 5.883-5.910 (m, 1H), 2.964-3.028 (m, 1H), 2.477-2.528 (m, 1H), 2.090 (s, 3H).

Example 6

(R)-2-(3-bromo-2-fluorophenyl)-4-hydroxycyclopent-2-enone

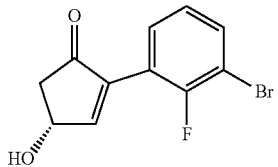 [SMILES: O=C1CC(O)C=C1c1cccc(Br)c1F]

Lipase-435 (3.0 g) was added to a solution of (R)-3-(3-bromo-2-fluorophenyl)-4-oxocyclopent-2-en-1-yl acetate (15 g, 48 mmol, from Example 5) in methyl isobutyl ketone (MIBK, 150 mL). The reaction mixture was stirred at room temperature for four hours. The Lipase-435 was filtered from the reaction mixture, and the filtrate was concentrated to obtain the crude compound. The crude product was purified by chromatography on silica gel using a mixture of hexane and ethyl acetate as a gradient eluent. Yield of the title compound was 10.65 g (83%).

$^1$H-NMR (400 MHz, CDCl$_3$): δ 7.816-7.828 (m, 1H), 7.707-7.747 (m, 1H), 7.509-7.549 (m, 1H), 7.035-7.075 (m, 1H), 5.103-5.118 (m, 1H), 2.934-2.995 (m, 1H), 2.458-2.510 (m, 1H).

Example 7

(4R)-2-(3-bromo-2-fluorophenyl)-4-((tetrahydro-2H-pyran-2-yl)oxy)cyclopent-2-enone

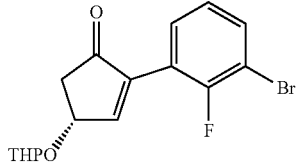

(R)-2-(3-bromo-2-fluorophenyl)-4-hydroxycyclopent-2-enone (10.0 g, 37 mmol, from Example 6) was dissolved with dichloromethane (100 mL). Then acetic acid (145 mg, 1.85 mmol) and dihydropyridine (4.67 g, 55.5 mmol) were added thereto. The reaction mixture was stirred at room temperature. The completion of reaction was confirmed by TLC monitor. The reaction mixture was quenched with 10% NaHCO$_{3(aq)}$ (100 mL) and the reaction mixture was phase separated. The organic layer was collected and dried over anhydrous Na$_2$SO$_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 10.99 g (83%).

$^1$H-NMR (400 MHz, CDCl$_3$): δ 7.873-7.927 (m, 1H), 7.715-7.771 (m, 1H), 7.503-7.524 (m, 1H), 7.016-7.055 (m, 1H), 5.001-5.030 (m, 1H), 4.790-4.868 (m, 1H), 3.853-3.994 (m, 1H), 3.532-3.585 (m, 1H), 2.856-2.965 (td, 1H, J=6.4, 18.8 Hz), 2.477-2.649 (m, 1H), 1.521-1.844 (m, 6H)

Example 8

(R-2-(3-bromo-2-fluorophenyl)-4-((tert-butyldimethylsilyl)oxy)cyclopent-2-enone

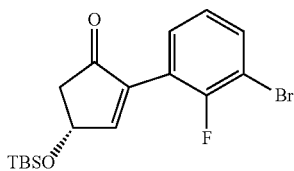 [SMILES: CC(C)(C)[Si](C)(C)O[C@H]1C=C(c2cccc(Br)c2F)C(=O)C1]

(R)-2-(3-bromo-2-fluorophenyl)-4-hydroxycyclopent-2-enone (1.5 g, 5.53 mmol, from Example 6) was dissolved with dichloromethane (15 mL). Then imidazole (0.75 g, 11.01 mmol) and tert-butyldimethylsilyl chloride (1.25 g, 8.23 mmol) were added thereto. The reaction mixture was stirred at room temperature. The completion of reaction was confirmed by TLC monitor. The reaction mixture was quenched with 10% NaHCO$_{3(aq)}$ (100 mL) and the reaction mixture was phase separated. The organic layer was collected and dried over anhydrous Na$_2$SO$_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 1.64 g (77%).

$^1$H-NMR (400 MHz, CDCl$_3$): δ 7.741-7.787 (m, 2H), 7.509-7.550 (m, 1H), 7.042-7.084 (m, 1H), 5.051-5.078 (m, 1H), 2.880-2.941 (m, 1H), 2.438-2.489 (m, 1H), 0.931 (s, 9H), 0.157-0.176 (m, 6H)

Example 9

(R)-methyl 4-(3-(3-((tert-butyldimethylsilyl)oxy)-5-oxocyclopent-1-en-1-yl)-2-fluorophenyl) Butanoate

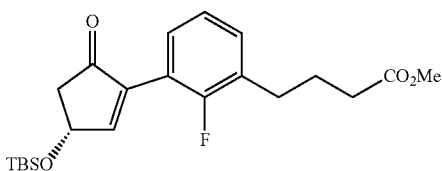 [SMILES: COC(=O)CCCc1cccc(C2=C[C@H](O[Si](C)(C)C(C)(C)C)CC2=O)c1F]

To a solution of methyl 3-butenoate (261 mg, 2.60 mmol) in dry THF (2.6 mL) was added dropwise 0.5 M (5.2 mL, 2.60 mmol) 9-BBN in THF at 0° C. under nitrogen. The reaction mixture was allowed to warm-up to room temperature and stirred for three hours. Then, the solution was transferred via cannula into a mixture of (R)-2-(3-bromo-2-fluorophenyl)-4-((tert-butyldimethylsilyl)oxy)cyclopent-2-enone (500 mg, 1.28 mmol, from example 8), Ph$_3$As (40 mg, 0.13 mmol), K$_3$PO$_4$ (827 mg, 3.90 mmol) and PdCl$_2$ (dppt) (95 mg, 0.13 mmol) in dry THF (5 mL) under nitrogen. The reaction mixture was stirred at 60° C. for three hours. The mixture was quenched by hydrogen peroxide (30% aqueous solution, 7.8 mmol) and stirred at 0° C. for 30 min. The reaction mixture was phase separated and the aqueous layer was extracted with ethyl acetate. The organic layers were combined and dried over anhydrous Na$_2$SO$_4$. The solid was filtered off and the organic solvent was evaporated off under vacuum. The crude product was purified by chromatography on silica gel using a mixture of hexane and ethyl acetate as a gradient eluent. Yield of the title compound was 211 mg (40%).

$^1$H-NMR (400 MHz, CDCl$_3$): δ 7.688-7.699 (m, 1H), 7.591-7.627 (m, 1H), 7.150-7.184 (m, 1H), 7.068-7.106 (m, 1H), 5.037-5.064 (m, 1H), 3.661 (s, 3H), 2.867-2.927 (m, 1H), 2.685-2.724 (m, 2H), 2.429-2.480 (m, 1H), 2.329-2.366 (m, 2H), 1.933-1.990 (m, 2H), 0.931 (s, 9H), 0.050-0.166 (m, 6H).

Example 10

(2SR,3RS,4RS)-2-(3-bromo-2-fluorophenyl)-3-((E)-3-((tert-butyldimethylsilyl)oxy)-4-methyloct-1-en-6-yn-1-yl)-4-((tetrahydro-2H-pyran-2-yl)oxy)cyclopentenone

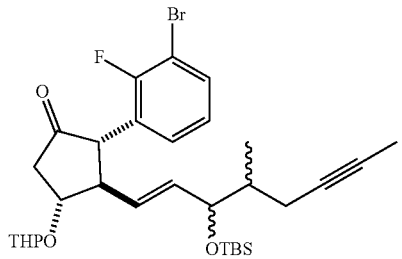

To a solution of (E)-tert-butyl((1-iodo-4-methyloct-1-en-6-yn-3-yl)oxy)dimethylsilane (130.0 g, 343.6 mmol) in dry diethyl ether (1000 mL) was added dropwise 1.9M (360 mL, 684 mmol) tert-butyllithium in pentane at −70° C. and was stirred for 2 hours at the same temperature. A mixture of copper iodide (65.3 g, 342.8 mmol) and n-tributylphosphine (180.7 g, 893.1 mmol) in THF (1.3 L) was cooled down to −70° C. and added to the reaction flask. After 1 hr. a solution of 2-(3-bromo-2-fluorophenyl)-4-((tetrahydro-2H-pyran-2-yl)oxy)cyclopent-2-enone (91.5 g, 257.6 mmol, from Example 4) in 90 ml THF at −70° C. was added thereto. The reaction mixture was quenched with saturated aqueous ammonium chloride (4.5 L) containing ammonium hydroxide (0.5 L). The reaction mixture was phase separated and the aqueous layer was extracted with ethyl acetate. The organic layers were combined and dried over anhydrous Na$_2$SO$_4$. The solid was filtered off and the organic solvent was evaporated under vacuum to give 426.6 g of the crude title compound.

Example 11

(1SR,2SR,3RS,4RS)-2-(3-bromo-2-fluorophenyl)-3-((E)-3-((tert-butyldimethylsilyl)oxy)-4-methyloct-1-en-6-yn-1-yl)-4-((tetrahydro-2H-pyran-2-yl)oxy) cyclopentanol

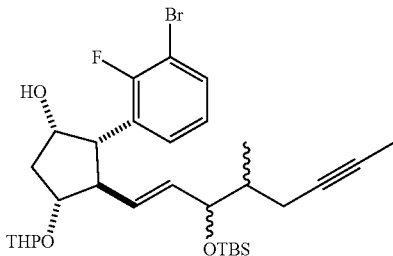

(2SR,3RS,4RS)-2-(3-bromo-2-fluorophenyl)-3-((3S,E)-3-((tert-butyldimethylsilyl)oxy)-4-methyloct-1-en-6-yn-1-yl)-4-((tetrahydro-2H-pyran-2-yl)oxy)cyclopentenone (426.6 g, 699.7 mmol, crude product from Example 10) was diluted with dry THF (4.3 L), then the solution was cooled to −70° C. and following by addition of 1.0M L-selectride (258 mL, 258 mole) in hexane at −70° C. After addition, the reaction was checked by TLC. The mixture was quenched by hydrogen peroxide (30% aqueous solution, 100 mL) and stirred at 0° C. for 30 min. The reaction mixture was phase separated and the aqueous layer was extracted with ethyl acetate. The organic layers were combined and dried over anhydrous $Na_2SO_4$. The solid was filtered off and the organic solvent was evaporated off under vacuum. The crude product was purified by chromatography on silica gel using a mixture of hexane and ethyl acetate as a gradient eluent. Yield of the title compound was 99.8 g (64%, 2 steps start from example 10).

$^1$H-NMR (400 MHz, $CDCl_3$): δ 7.422 (m, 1H), 7.258-7.338 (m, 11H), 6.991-7.021 (m, 1H), 5.364-5.553 (m, 2H), 4.702-4.747 (m, 1H), 3.854-4.285 (m, 4H), 3.493-3.519 (m, 1H), 3.116-3.221 (m, 2H), 2.395-2.564 (m, 1H), 1.541-2.110 (m, 1H), 0.647-0.910 (m, 12H), −0.271~−0.026 (m, 6H).

Example 12

(((E)-1-((1RS,2RS,3aSR,8bSR)—S-bromo-2-((tetrahydro-2H-pyran-2-yl)oxy)-2,3,3a,8b-tetrahydro-1H-cyclopenta[b]benzofuran-1-yl)-4-methyloct-1-en-6-yn-3-yl)oxy)(tert-butyl)dimethylsilane

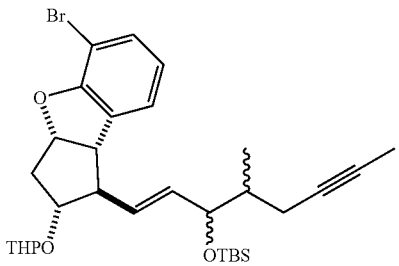

To a solution of (1SR,2SR,3RS,4RS)-2-(3-bromo-2-fluorophenyl)-3-((E)-3-((tert-butyldimethylsilyl)oxy)-4-methyl-oct-1-en-6-yn-1-yl)-4-((tetrahydro-2H-pyran-2-yl)oxy)cyclopentanol (98.3 g, 166.7 mmol, from Example 11) in toluene (5.45 L) and DMPU (115.4 g, 900.3 mmol) was added t-BuOK (64.3 g, 573.1 mmol) under nitrogen at 60° C. The completion of reaction was confirmed by TLC monitor. The mixture was washed by saturated aqueous ammonium chloride (1000 mL) and dried over anhydrous $Na_2SO_4$. The solid was filtered off and the organic solvent was evaporated off under vacuum. The crude product was purified by chromatography on silica gel using a mixture of hexane and ethyl acetate as a gradient eluent. Yield of the title compound was 79.2 g (83%).

$^1$H-NMR (400 MHz, $CDCl_3$): δ 7.259 (m, 11H), 7.054 (m, 1H), 6.686-6.714 (m, 1H), 5.521-5.655 (m, 2H), 5.262-5.294 (m, 1H), 4.603-4.662 (m, 1H), 4.049-4.184 (m, 2H), 3.837-3.912 (m, 1H), 3.411-3.689 (m, 2H), 2.441-2.781 (m, 2H), 1.947-2.242 (m, 3H), 1.209-1.785 (m, 10H), 0.833-0.939 (m, 12H), 0.101-0.070 (m, 6H).

Example 13

(1RS,2RS,3aSR,8bSR)-5-bromo-1-((3SR,E)-3-hydroxy-4-methyloct-1-en-6-yn-1-yl)-2,3,3a,8b-tetrahydro-1H-cyclopenta[h]benzofuran-2-ol

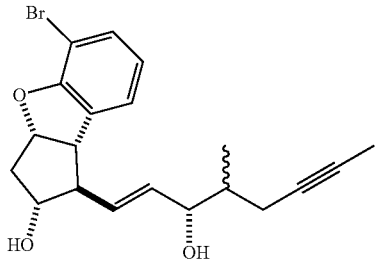 [SMILES: CC#CCC(C)[C@H](O)/C=C/[C@@H]1[C@H]2c3cccc(Br)c3O[C@H]2C[C@H]1O]

(((E)-1-((1RS,2RS,3aSR,8bSR)-5-bromo-2-((tetrahydro-2H-pyran-2-yl)oxy)-2,3,3a,8b-tetrahydro-1H-cyclopenta[b]benzofuran-1-yl)-4-methyloct-1-en-6-yn-3-yl)oxy)(tert-butyl)dimethylsilane (75.8 g, 128.5 mmol, from Example 12) was diluted with acetonitrile (758 mL), and 3N aqueous HCl (76 mL) was added thereto. The mixture was stirred at room temperature and the progress of reaction was check by TLC. After the completion of reaction, the mixture was neutralized with 10% aqueous $NaHCO_3$ (760 mL) to pH 7-8 and then concentrated to remove acetonitrile. The residue was extracted with ethyl acetate and the organic layer was dried over anhydrous $Na_2SO_4$. The solid was filtered off and the organic solvent was evaporated off under vacuum. The crude product was purified by chromatography on silica gel using a mixture of hexane and ethyl acetate as a gradient eluent. Yield of the title 11,15-Syn isomers was 26.3 g (52%) and 11,15-Anti isomers (15-epi isomer) was 11.1 g (22%). The compound was recrystallized from a solvent mixture of ethyl acetate and n-hexane to obtain the crystal compound (22.83 g). The crystal compound was characterized by X-ray powder diffraction (XRPD) pattern with peaks at 6.7±0.2°, 15.4±0.2°. 19.5±0.2°, 19.9±0.2°, and 21.5±0.2°, 2θ.

$^1$H-NMR (400 MHz, $CDCl_3$): δ 7.259-7.294 (m, 1H), 6.992-7.032 (m, 1H), 6.698-6.730 (m, 1H), 5.563-5.706 (m, 2H), 5.186-5.235 (m, 1H), 4.029-4.194 (m, 1H), 3.924 (m, 11H), 3.505-3.544 (m, 11H), 2.655-2.722 (m, 1H), 2.426-2.482 (m, 1H), 2.235-2.267 (m, 2H), 2.013-2.101 (m, 1H), 1.734-1.825 (m, 4H), 0.977-1.019 (m, 3H).

Example 14

Methyl 4-((1RS,2RS,3aSR,8bSR)-2-hydroxy-1-((3SR,E)-3-hydroxy-4-methyloct-1-en-6-yn-1-yl)-2,3,3a,8b-tetrahydro-1H-cyclopenta[b]benzofuran-5-yl)butanoate

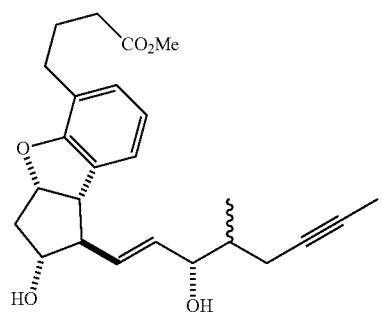 [SMILES: CC#CCC(C)[C@H](O)/C=C/[C@@H]1[C@H]2c3cccc(CCCC(=O)OC)c3O[C@H]2C[C@H]1O]

To a solution of methyl 3-butenoate (2.9 g, 28.9 mmol) in dry THF (30 mL) was added dropwise 0.5 M (56.2 mL, 28.1 mmol) 9-BBN in THF at 0° C. under nitrogen. The reaction mixture was allowed to warm-up to room temperature and was kept stirring for three hours. Then, the solution was transferred via cannula into a mixture of (1RS,2RS,3aSR,8bSR)-5-bromo-1-((3SR,E)-3-hydroxy-4-methyloct-1-en-6-yn-1-yl)-2,3,3a,8b-tetrahydro-1H-cyclopenta[b]benzofuran-2-ol (5.0 g, 12.8 mmol, from example 13). $Ph_3As$ (390 mg, 1.3 mmol), $K_3PO_4$ (8.14 g, 38.3 mmol) and $PdCl_2$(dppf)-$CH_2Cl_2$ (1.04 g, 1.3 mmol) in dry THF (50 mL) under nitrogen. The reaction mixture was stirred at 60° C. for three hours. After the completion of reaction, the mixture was quenched by hydrogen peroxide (30% aqueous solution, 20 mL) and was kept stirring at 0° C. for 30 min. Follow by add the saturated aqueous ammonium chloride (250 mL) into reactor, then the reaction mixture was phase separated and the aqueous layer was extracted with ethyl acetate. The organic layers were combined and dried over anhydrous $Na_2SO_4$. The solid was filtered off and the organic solvent was evaporated off under vacuum. The crude product was purified by chromatography on silica gel using a mixture of hexanes and ethyl acetate as a gradient eluent. Yield of the title compound was 3.74 g (71%).

$^1$H-NMR (400 MHz, $CDCl_3$): δ 6.940 (m, 2H), 6.758 (m, 1H), 5.558-5.708 (m, 2H), 5.087 (m, 1H), 4.045-4.173 (m, 1H), 3.913 (m, 1H), 3.649 (s, 3H), 3.411-3.454 (m, 1H), 2.483-2.649 (m, 3H), 2.384-2.434 (m, 1H), 2.243-2.366 (m, 5H), 1.862-2.088 (m, 3H), 1.717-1.829 (m, 4H), 0.824-1.030 (m, 3H)

Example 15

4-((1RS,2RS,3aSR,8bSR)-2-hydroxy-1-((3SR,E)-3-hydroxy-4-methyloct-1-en-6-yn-1-yl)-2,3,3a,8b-tetrahydro-1H-cyclopenta[b]benzofuran-5-yl)butanoic acid (Beraprost)

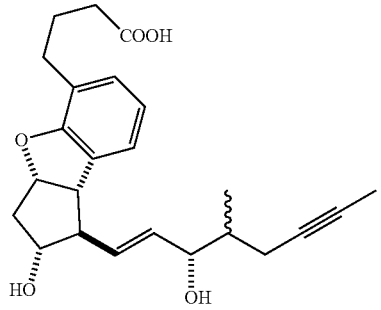

Methyl 4-((1RS,2RS,3aSR,8bSR)-2-hydroxy-1-((3SR,E)-3-hydroxy-4-methyloct-1-en-6-yn-1-yl)-2,3,3a,8b-tetrahydro-1H-cyclopenta[b]benzofuran-5-yl)butanoate (2.38 g, 5.97 mmol) was dissolved in methanol (24 mL) and a solution of NaOH (460 mg, 11.5 mmol) in water (24 mL) was added dropwise slowly thereto at 10° C. After the completion of reaction, the methanol was removed from reaction mixture in vacuum. The residue was diluted with water (25 mL) and further washed with methyl-tert-butyl ether (25 mL). The aqueous layer was acidified with 3N aqueous HCl to pH 3-4 and further extracted with methyl-tert-butyl ether (25 mL). The organic layer was dried over anhydrous Na2SO4. The solid was filtered off and the organic solvent was evaporated off under vacuum. The crude product was purified by chromatography on silica gel using a mixture of hexane and ethyl acetate as a gradient eluent.

Yield of the title compound was 1.78 g (77%).

$^1$H-NMR (400 MHz, $CDCl_3$): δ 6.892-6.942 (m, 2H), 6.729-6.748 (m, 1H), 5.503-5.656 (m, 2H), 5.038-5.056 (m, 1H), 3.984-4.107 (m, 1H), 3.821-3.893 (m, 1H), 3.214-3.390 (m, 1H), 2.542-2.673 (m, 3H), 2.325-2.394 (m, 3H), 2.044-2.238 (m, 2H), 1.857-1.998 (m, 3H), 1.745-1.788 (m, 4H), 0.979-1.031 (d, 3H).

$^{13}$C-NMR (100 MHz, $CDCl_3$): δ 178.685, 157.204, 134.016, 133.811, 133.325, 132.756, 129.621, 129.576, 128.908, 123.200, 123.169, 121.856, 121.811, 120.551, 120.513, 84.223, 84.132, 77.415, 77.240, 77.225, 77.179, 76.367, 76.079, 75.980, 58.780, 58.735, 50.196, 50.150, 41.103, 38.218, 38.066, 33.209, 29.034, 24.540, 22.453, 22.362, 15.720, 14.847, 3.523, 3.492.

Example 16

(2S,3R,4R)-2-(3-bromo-2-fluorophenyl)-3-((3S,4S,E)-3-((tert-butyldimethylsilyl)oxy)-4-methyloct-1-en-6-yn-1-yl)-4-((tetrahydro-2H-pyran-2-yl)oxy)cyclopentanone

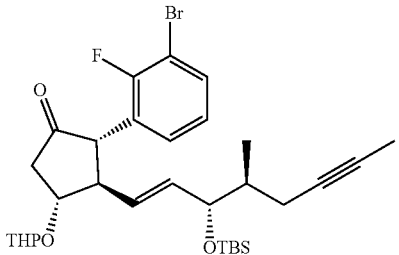

A 2-thienyl(cyano)copper lithium was prepared under dry Nitrogen. To a solution of thiophene (6.84 g, 81.4 mmol) in dry THF (70 mL) was added dropwise 1.6 M n-butyllithium in hexane (46.3 mL, 74.1 mmol) at −10° C. After one hour, the reaction mixture was cooled to −70° C. The solution was transferred via cannula into a suspension of copper cyanide (7.3 g, 81.5 mmol) in dry THE (73 mL) at −70° C. and was stirred for 30 min. Then, n-butyllithium in hexane (1.6M, 55.5 mL, 88.8 mmol) was added dropwisely to a solution of tert-butyldimethyl(((3S,4S,E)-4-methyl-1-(tributylstannyl)oct-1-en-6-yn-3-yl)oxy)silane (40.1 g, 74 mmol) at −70° C. for 30 min. The 2-thienyl(cyano)copper lithium was added to the reaction mixture via cannula at −70° C. and was stirred for 30 min. Then, a solution of (4R)-2-(3-bromo-2-fluorophenyl)-4-((tetrahydro-2H-pyran-2-yl)oxy)cyclopent-2-enone (13.2 g, 37.1 mmol, from Example 7) was added thereto. The reaction mixture was quenched with saturated aqueous ammonium chloride (540 mL) containing ammonium hydroxide (60 mL). The reaction mixture was phase separated and the aqueous layer was extracted with ethyl acetate. The organic layers were combined and dried over anhydrous Na$_2$SO$_4$. The solid was filtered off and the organic solvent was evaporated under vacuum to give 60.2 g of the crude title compound.

Example 17

(1S,2S,3R,4R)-2-(3-bromo-2-fluorophenyl)-3-((3S,4S,E)-3-((tert-butyldimethylsilyl)oxy)-4-methyloct-1-en-6-yn-1-yl)-4-((tetrahydro-2H-pyran-2-yl)oxy)cyclopentanol

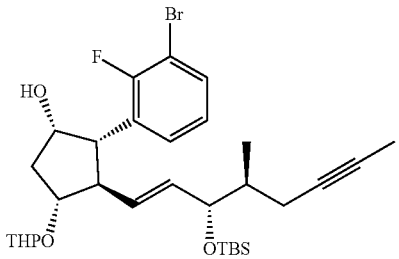

The compound was obtained from (2S,3R,4R)-2-(3-bromo-2-fluorophenyl)-3-((3S,4S,E)-3-((tert-butyldimeth-ylsilyl)oxy)-4-methyloct-1-en-6-yn-1-yl)-4-((tetrahydro-2H-pyran-2-yl)oxy)cyclopentenone (60.2 g, from Example 16) by following the procedure of Example 11. Yield of the title compound was 13.8 g (65%, 2 steps from Example 16).

$^1$H-NMR (400 MHz, CDCl$_3$): δ 7.422 (m, 1H), 7.289-7.352 (m, 1H), 7.001 (m, 1H), 5.359-5.542 (m, 2H), 4.699-4.743 (m, 11H), 3.850-4346 (m, 4H), 3.497-3.513 (m, 1H), 3.130-3.265 (m, 2H), 2.378-2.578 (m, 1H), 1.524-2.026 (m, 14H), 0.642-0.955 (m, 12H), −0.182-0.089 (m, 6H).

Example 18

(((3S,4S,E)-1-((1R,2R,3aS,8bS)-5-bromo-2-((tetrahydro-2H-pyran-2-yl)oxy)-2.3.3a,8b-tetrahydro-1H-cyclopenta[b]benzofuran-1-yl)-4-methyloct-1-en-6-yn-3-yl)oxy)(tert-butyl)dimethylsilane

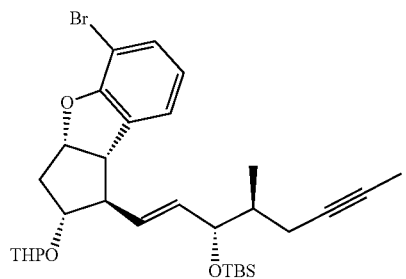

The compound was obtained from (1S,2S,3R,4R)-2-(3-bromo-2-fluorophenyl)-3-((3S,4S,E)-3-((tert-butyldimethylsilyl)oxy)-4-methyloct-1-en-6-yn-1-yl)-4-((tetrahydro-2H-pyran-2-yl)oxy)cyclopentanol (13.8 g, 22.6 mmol, from example 17) by following the procedure of Example 12. Yield of the title compound was 10.9 g (81%).

$^1$H-NMR (400 MHz, CDCl$_3$): δ 7.259 (m, 1H), 7.014-7.055 (m, 11H), 6.670-6.689 (m, 1H), 5.481-5.654 (m, 2H), 5.242-5.264 (m, 11H), 4.603-4.664 (m, 11H), 4.048-4.077 (m, 2H), 3.818-3.912 (m, 1H), 3.414-3.713 (m, 2H), 2.408-2.798 (m, 2H), 2.057-2.233 (m, 3H), 1.259-1.787 (m, 10H), 0.856-0.950 (m, 12H), −0.007-0.095 (m, 6H).

Example 19

(1R,2R,3aS,8bS)-5-bromo-1-((3S,4S,E)-3-hydroxy-4-methyloct-1-en-6-yn-1-yl)-2,3,3a,8b-tetrahydro-1H-cyclopenta[b]benzofuran-2-ol

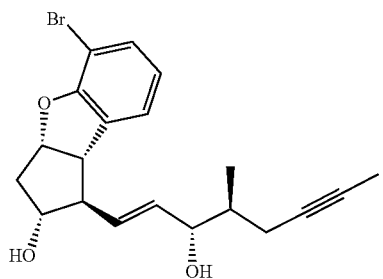 [SMILES: CC#CC[C@H](C)[C@H](O)/C=C/[C@@H]1[C@H]2c3cccc(Br)c3O[C@H]2C[C@H]1O]

The compound was obtained from (((3S,4S,E)-1-((1R,2R,3aS,8bS)-5-bromo-2-((tetrahydro-2H-pyran-2-yl)oxy)-2,3,3a,8b-tetrahydro-1H-cyclopenta[b]benzofuran-1-yl)-4-methyloct-1-en-6-yn-3-yl)oxy (tert-butyl)dimethylsilane (9.9 g, 16.8 mmol, from example 18) by following the procedure of Example 13. Yield of the title compound was 5.55 g (84%). The crystal compound was obtained (4.12 g, 75%) after recrystallization. The crystal compound was characterized by X-ray powder diffraction pattern with peaks at 6.7±0.2°, 15.4±0.2°. 19.5±0.2°, 19.9±0.2°, and 21.5±0.2°, 2θ.

$^1$H-NMR (400 MHz, CDCl$_3$): δ 7.258-7.277 (m, 1H), 6.967-6.985 (m, 11H), 6.681-6.720 (m, 1H), 5.523-5.655 (m, 2H), 5.158-5.213 (m, 1H), 3.989-4.024 (m, 1H), 3.838-3.884 (m, 1H), 3.463-3.508 (m, 1H), 3.285-3.296 (m, 1H), 2.949 (s, 1H), 2.665-2.733 (m, 1H), 2.343-2.407 (m, 1H), 2.221-2.242 (m, 2H), 1.972-2.044 (m, 1H), 1.715-1.853 (m, 4H), 0.961-0.977 (m, 311).

Example 20 methyl 4-((1R,2R,3aS,8bS)-2-hydroxy-1-((3S,4S,E)-3-hydroxy-4-methyloct-1-en-6-yn-1-yl)-2,3,3a,8b-tetrahydro-1H-cyclopenta[b]benzofuran-5-yl)butanoate

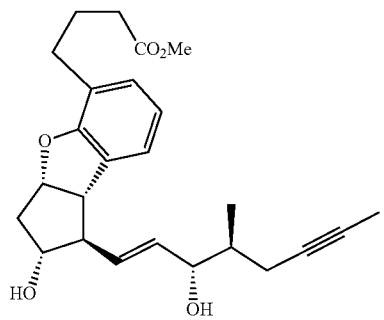 [SMILES: CC#CC[C@H](C)[C@H](O)/C=C/[C@@H]1[C@H]2c3cccc(CCCC(=O)OC)c3O[C@H]2C[C@H]1O]

The compound was obtained from (1R,2R,3aS,8bS)-5-bromo-1-((3S,4S,E)-3-hydroxy-4-methyloct-1-en-6-yn-1-yl)-2,3,3a,8b-tetrahydro-1H-cyclopenta[b]benzofuran-2-ol (2.0 g, 5.1 mmol, from Example 19) by following the procedure of Example 14. Yield of the title compound was 1.47 g (70%). The crystal compound was obtained (1.11 g, 75%) after recrystallization. The crystal compound was characterized by X-ray powder diffraction pattern with peaks at 8.2±0.2°, 10.8±0.2°, 18.5±0.2°, 20.9±0.2°, and 22.1±0.2°. 2θ.

$^1$H-NMR (400 MHz, CDCl$_3$): δ 6.886-6.931 (m, 2H), 6.711-6.748 (t, 1H), 5.501-5.656 (m, 2H), 5.015-5.070 (m, 1H), 3.969-4.007 (t, 1H), 3.809-3.869 (m, 1H), 3.628 (s, 3H), 3.541 (s, 1H), 3.341-3.386 (t, 1H), 3.168 (s, 1H), 2.564-2.677 (m, 3H), 2.291-2.373 (m, 3H), 2.168-2.220 (m, 2H), 1.876-1.970 (m, 3H), 1.696-1.778 (m, 4H), 0.955-0.971 (m, 3H).

$^{13}$C-NMR (100 MHz, CDCl$_3$); δ 174.173, 157.194, 134.083, 133.324, 129.582, 128.830, 123.290, 121.749, 120.428, 84.042, 77.279, 77.150, 76.285, 75.882, 58.843, 51.458, 50.129, 41.211, 38.175, 33.416, 29.173, 24.710, 22.358, 15.694, 3.474.

Example 21

4-((1R,2R,3aS,8bS)-2-hydroxy-1-((3S,4S,E)-3-hydroxy-4-methyloct-1-en-6-yn-1-yl)-2,3,3a,8b-tetrahydro-1H-cyclopenta[b]benzofuran-5-yl)butanoic acid (Beraprost-314d)

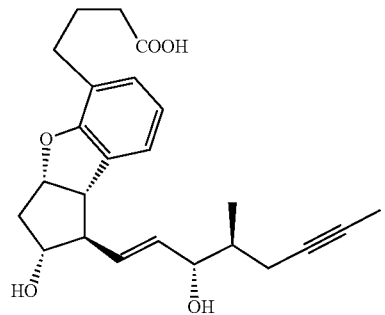 [SMILES: CC#CC[C@H](C)[C@H](O)/C=C/[C@@H]1[C@H]2c3cccc(CCCC(=O)O)c3O[C@H]2C[C@H]1O]

The compound was obtained from methyl 4-((1R,2R,3aS,8bS)-2-hydroxy-1-((3S,4S,E)-3-hydroxy-4-methyloct-1-en-6-yn-1-yl)-2,3,3a,8b-tetrahydro-1N-cyclopenta[b]benzofuran-5-yl)butanoate (406 mg, 0.98 mmol, from Example 20) by following the procedure of Example 15. Yield of the title compound was 353 mg (90%). The crystal compound was obtained (251 mg, 71%) after recrystallization. The crystal compound was characterized by X-ray powder diffraction pattern with peaks at 6.1±0.2°, 6.6±0.2°, 7.2±0.2°, 12.1±0.2°, and 16.3±0.2°, 2θ.

$^1$H-NMR (400 MHz, CDCl$_3$): δ 6.904-6.941 (m, 2H), 6.722-6.759 (t, 1H), 5.522-5.672 (m, 2H), 5.032-5.086 (m, 1H), 3.996-4.033 (m, 1H), 3.850-3.909 (m, 1H), 3.369-3.412 (m, 1H), 2.536-2.668 (m, 3H), 2.301-2.416 (m, 3H), 2.229 (m, 2H), 1.879-2.005 (m, 3H), 1.717-1.788 (m, 4H), 0.967-0.984 (d, 3H).

$^{13}$C-NMR (100 MHz, CDCl$_3$): δ 178.287, 157.194, 134.052, 133.293, 129.582, 128.937, 123.199, 121.810, 120.504, 84.148, 77.233, 77.218, 76.353, 75.966, 58.752, 50.137, 41.082, 38.061, 33.135, 29.022, 24.543, 22.342, 15.716, 3.519.

Example 22

Methyl 4-((1R,2R,3aS,8bS)-2-((tert-butyldimethylsilyl)oxy)-1-((3S,4S,E)-3-((tert-butyldimethylsilyl)oxy)-4-methyloct-1-en-6-yn-1-yl)-2,3,3a,8b-tetrahydro-1H-cyclopenta[b]benzofuran-5-yl)butanoate

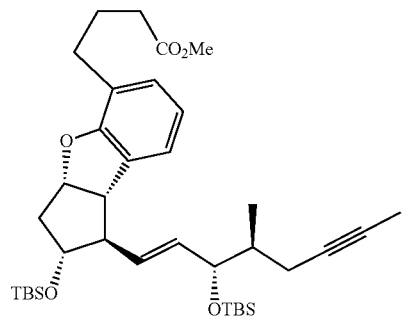 [SMILES: CC#CC[C@H](C)[C@@H](/C=C/[C@@H]1[C@H]2c3cccc(CCCC(=O)OC)c3O[C@H]2C[C@H]1O[Si](C)(C)C(C)(C)C)O[Si](C)(C)C(C)(C)C]

The compound was obtained from (R)-methyl 4-(3-(3-((tert-butyldimethylsilyl)oxy)-5-oxocyclopent-1-en-1-yl)-2-fluorophenyl) butanoate (10.0 g, 24.6 mmol, from Example 9) and tert-butyldimethyl(((3S,4SE)-4-methyl-1-(tributyl-stannyl)oct-1-en-6-yn-3-yl)oxy) silane (39.96 g, 73.8 mmol) followed by the same procedures of Examples 10, 11 and 12. Yield of the title compound was 7.6 g (48%, 3 steps).

¹H-NMR (400 MHz, CDCl₃): δ 6.963-6.982 (d, 1H), 6.895-6.912 (d, 1H), 6.708-6.745 (t, 1H, J=7.6 Hz), 5.496-5.623 (m, 2H), 5.073-5.126 (m, 1H), 4.019-4.048 (m, 1H), 3.902-3.952 (m, 1H), 3.652 (s, 3H), 3.433-3.473 (m, 1H), 2.525-2.599 (m, 3H), 2.417-2.484 (m, 1H), 2.319-2.356 (m, 2H), 2.192-2.252 (m, 1H), 2.060-2.120 (m, 1H), 1.891-2.012 (m, 3H), 1.780-1.792 (m, 3H), 1.628-1.745 (m, 1H), 0.758-0.941 (m, 21H), −0.049-0.091 (m, 12H).

¹³C-NMR (100 MHz, CDCl₃): δ 174.105, 157.331, 132.861, 131.350, 130.212, 128.405, 122.956, 121.901, 120.109, 84.801, 77.909, 77.142, 76.421, 75.958, 58.114, 51.412, 49.962, 42.380, 39.746, 33.568, 29.302, 29.234, 25.887, 25.674, 25.629, 24.756, 21.940, 18.168, 17.819, 15.542, 3.458, −2.970, −3.980, −4.678, −4.875.

What is claimed is:

1. An optically enriched compound of Formula 4a":

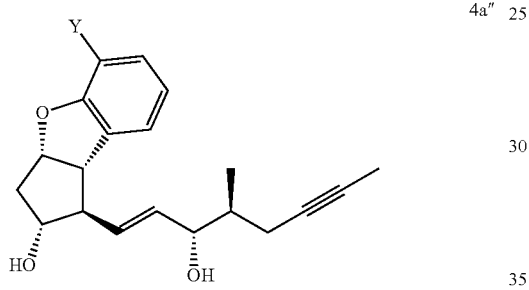

4a"

wherein Y is Cl, Br, or I.

2. The compound according to claim 1, wherein Y is Br.

3. A racemic mixture of Formula 11,15-Syn 4b":

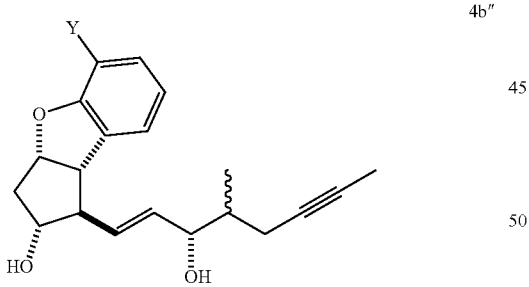

4b"

11,15-Syn wherein Y is Cl, Br, or I.

4. The compound according to claim 3, comprising four isomers of Formula 4b"-1, Formula 4b"-2, Formula 4b"-3, and Formula 4b"-4

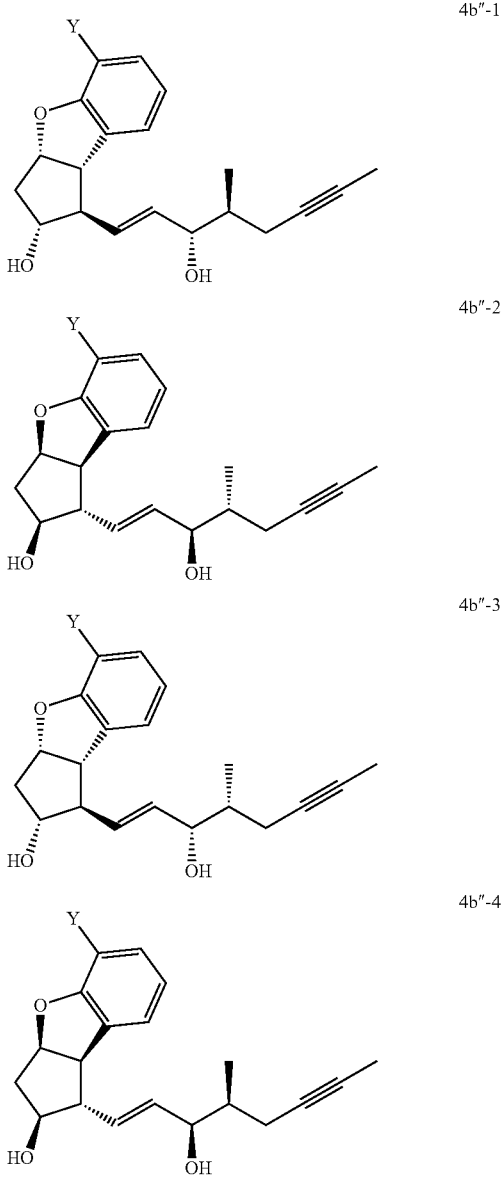

wherein Y is Cl, Br, or I.

* * * * *